(12) United States Patent
Pesach

(10) Patent No.: US 10,136,970 B2
(45) Date of Patent: Nov. 27, 2018

(54) SYSTEM, DEVICE, AND METHOD FOR DENTAL INTRAORAL SCANNING

(71) Applicant: DENTLYTEC G.P.L. LTD., Tel-Aviv (IL)

(72) Inventor: Benny Pesach, Rosh HaAyin (IL)

(73) Assignee: DENTLYTEC G.P.L.LTD, Tel-Aviv (IL)

( * ) Notice: Subject to any disclaimer, the term of this patent is extended or adjusted under 35 U.S.C. 154(b) by 0 days.

(21) Appl. No.: 15/115,196

(22) PCT Filed: Jan. 18, 2016

(86) PCT No.: PCT/IL2016/050058
§ 371 (c)(1),
(2) Date: Jul. 28, 2016

(87) PCT Pub. No.: WO2016/113745
PCT Pub. Date: Jul. 21, 2016

(65) Prior Publication Data
US 2016/0338803 A1 Nov. 24, 2016

Related U.S. Application Data

(60) Provisional application No. 62/104,835, filed on Jan. 18, 2015.

(51) Int. Cl.
*G06T 1/00* (2006.01)
*A61C 9/00* (2006.01)
(Continued)

(52) U.S. Cl.
CPC .............. *A61C 9/006* (2013.01); *A61B 1/06* (2013.01); *A61B 1/24* (2013.01); *A61C 3/02* (2013.01);
(Continued)

(58) Field of Classification Search
None
See application file for complete search history.

(56) References Cited

U.S. PATENT DOCUMENTS 4,571,180 A 2/1986 Kulick
4,873,651 A * 10/1989 Raviv .................. G06T 1/0014
250/224
(Continued)

FOREIGN PATENT DOCUMENTS

CN 101677757 3/2010
EP 2165674 A1 3/2010
(Continued)

OTHER PUBLICATIONS

Bouguet, "3D photography using shadows in dual-space geometry," International Journal of Computer Vision, vol. 35 No. 2 (1999).*
(Continued)

*Primary Examiner* — Jayanti K Patel
*Assistant Examiner* — Shadan E Haghani
(74) *Attorney, Agent, or Firm* — Cooley LLP

(57) ABSTRACT

There is provided according to some embodiments, a system, device and method for a three dimensional (3D) intraoral scanning of at least a portion of a tooth. An intraoral scanner may include a shadow casting object extending between a light emitter and the portion of the tooth. An imaging module may image the portion of the tooth and/or the projected shadow of the shadow casting object. A method to construct a 3D model may include illuminating at least a portion of the tooth with a light emitter; casting a shadow on the portion of the tooth by an object located between the emitter and the tooth; imaging the portion of the tooth, including at least a part of the shadow; and determining a location of a point on the tooth and related to the shadow, using the image.

30 Claims, 20 Drawing Sheets

(51) Int. Cl.
| | |
|---|---|
| *G06T 15/60* | (2006.01) |
| *G06T 17/00* | (2006.01) |
| *A61B 1/06* | (2006.01) |
| *A61B 1/24* | (2006.01) |
| *A61C 3/02* | (2006.01) |
| *A61C 19/04* | (2006.01) |
| *G06T 7/20* | (2017.01) |
| *H04N 5/225* | (2006.01) |
| *G06T 7/73* | (2017.01) |
| *G06T 7/13* | (2017.01) |

(52) U.S. Cl.
CPC ............ *A61C 19/04* (2013.01); *G06T 1/0007* (2013.01); *G06T 7/13* (2017.01); *G06T 7/20* (2013.01); *G06T 7/74* (2017.01); *G06T 15/60* (2013.01); *G06T 17/00* (2013.01); *H04N 5/2256* (2013.01); *A61C 9/008* (2013.01); *G06T 2200/08* (2013.01); *G06T 2207/10028* (2013.01); *G06T 2207/30036* (2013.01); *G06T 2210/41* (2013.01); *H04N 2005/2255* (2013.01)

(56) References Cited

U.S. PATENT DOCUMENTS

| | | | | |
|---|---|---|---|---|
| 5,051,823 | A * | 9/1991 | Cooper | A61B 1/00096 348/66 |
| 5,224,049 | A | 6/1993 | Mushabac | |
| 5,257,184 | A | 10/1993 | Mushabac | |
| 5,313,053 | A * | 5/1994 | Koenck | B60R 11/02 235/470 |
| 5,320,462 | A | 6/1994 | Johansson et al. | |
| 5,372,502 | A | 12/1994 | Massen et al. | |
| 5,850,289 | A * | 12/1998 | Fowler | G01B 11/08 250/559.22 |
| 5,897,509 | A | 4/1999 | Toda et al. | |
| 5,919,129 | A | 7/1999 | Vandre | |
| 5,969,321 | A * | 10/1999 | Danielson | G06K 7/10574 235/462.01 |
| 5,993,209 | A | 11/1999 | Matoba et al. | |
| 6,468,079 | B1 | 10/2002 | Fischer et al. | |
| 6,885,464 | B1 | 4/2005 | Pfeiffer et al. | |
| 7,346,417 | B2 | 3/2008 | Lüth et al. | |
| 7,494,338 | B2 | 2/2009 | Durbin et al. | |
| 7,625,335 | B2 | 12/2009 | Deichmann et al. | |
| 7,813,591 | B2 | 10/2010 | Paley et al. | |
| 8,744,194 | B2 | 6/2014 | Kawasaki et al. | |
| 2006/0154198 | A1 | 7/2006 | Durbin et al. | |
| 2007/0064242 | A1* | 3/2007 | Childers | G01B 11/24 356/601 |
| 2007/0065782 | A1 | 3/2007 | Maschke | |
| 2007/0172112 | A1 | 7/2007 | Paley et al. | |
| 2008/0002869 | A1 | 1/2008 | Scharlack et al. | |
| 2008/0160477 | A1 | 7/2008 | Stookey et al. | |
| 2008/0201101 | A1* | 8/2008 | Hebert | G01B 11/245 702/152 |
| 2008/0261165 | A1 | 10/2008 | Steingart et al. | |
| 2009/0017416 | A1 | 1/2009 | Nguyen et al. | |
| 2009/0087050 | A1 | 4/2009 | Gandyra | |
| 2010/0189341 | A1 | 7/2010 | Oota et al. | |
| 2010/0238279 | A1 | 9/2010 | Thoms et al. | |
| 2010/0268069 | A1 | 10/2010 | Liang | |
| 2010/0268071 | A1 | 10/2010 | Kim | |
| 2010/0305435 | A1 | 12/2010 | Magill | |
| 2012/0015329 | A1 | 1/2012 | Gross et al. | |
| 2012/0040305 | A1* | 2/2012 | Karazivan | A61B 1/00087 433/29 |
| 2012/0046536 | A1 | 2/2012 | Cheung et al. | |
| 2012/0097002 | A1 | 4/2012 | Thiedig | |
| 2012/0271176 | A1 | 10/2012 | Moghaddam et al. | |
| 2013/0027515 | A1* | 1/2013 | Vinther | A61B 1/00177 348/44 |
| 2013/0273492 | A1 | 10/2013 | Suttin, Sr. et al. | |
| 2014/0066784 | A1 | 3/2014 | Yokota | |
| 2014/0093835 | A1* | 4/2014 | Levin | A61B 5/0088 433/29 |
| 2014/0199650 | A1 | 7/2014 | Moffson et al. | |
| 2014/0221819 | A1* | 8/2014 | Sarment | A61B 5/064 600/424 |
| 2014/0309523 | A1 | 10/2014 | Daon et al. | |
| 2014/0343395 | A1 | 11/2014 | Choi et al. | |
| 2015/0348320 | A1 | 12/2015 | Pesach et al. | |
| 2017/0007377 | A1 | 1/2017 | Pesach et al. | |

FOREIGN PATENT DOCUMENTS

| | | |
|---|---|---|
| FR | 2692773 A1 | 12/1993 |
| JP | H10262996 | 10/1998 |
| JP | 2003-325451 | 11/2003 |
| JP | 2007-152004 | 6/2007 |
| JP | 2009-268614 | 11/2009 |
| JP | 2010-104652 | 5/2010 |
| JP | 2012-016573 | 1/2012 |
| JP | 2014-236957 | 12/2014 |
| WO | WO 1998/006352 A1 | 2/1998 |
| WO | WO 2014/020247 A1 | 2/2014 |
| WO | WO 2014/102779 | 7/2014 |
| WO | WO 2015/107520 | 7/2015 |
| WO | WO 2016/110855 | 7/2016 |
| WO | WO 2016/113745 | 7/2016 |
| WO | WO 2016/178212 | 11/2016 |

OTHER PUBLICATIONS

Bouguet, "3D photography using shadows in dual-space geometry," International Journal of COmputer Vision vol. 35 No. 2 pp. 129-149 (Nov./Dec. 1999).*
Goshtasby, "A System for Digital Reconstruction of Gypsum Dental Casts," IEEE Transaction on Medical Imaging (1997).*
Notification of Office Action dated Apr. 15, 2016 From the State Intellectual Property Office of the People's Republic of China Re. Application No. 201380071840.0.
Translation of Notification dated Apr. 15, 2016 From the State Intellectual Property Office of the People's Republic of China Re. Application No. 201380071840.0.
International Search Report and the Written Opinion dated Aug. 23, 2016 From the International Searching Authority Re. Application No. PCT/IL2016/050449.
International Search Report and Written Opinion dated Apr. 18, 2016 for PCT/IL2016/050058, filed Jan. 18, 2016.
Flügge, et al., "Precision of Intraoral Digital Dental Impressions with iTero and Extraoral Digitization With the iTero and a Model Scanner," American Journal of Orthodontics and Dentofacial Orthopedics, 144(3); 471-478; Sep. 2013.
Logozzo et al., "Recent Advances in Dental Optics—Part I: 3D Intraoral Scanners for Restorative Dentistry", Optics and Lasers in Engineering, 54: 203-221, Mar. 2014.
Salvi, et al., "Pattern Codification Strategies in Structured Light Systems", Pattern Recognition, 37(4): 827-849, 2004.
Savarese et al., "3D Reconstruction by Shadow Carving: Theory and Practical Evaluation", International Journal of Computer Vision, 71(3): 305-336, published online, Jun. 2006.
Maintz et al., "A Survey of Medical Image Registration," Medical Image Analysis, 2(1): 1-36, Mar. 1998.
Medeiros, et al., "Coded Structured Light for 3D-Photography: An Overview", IEEE-RITA, (Latin-American Learning Technologies Journal), IV(2): 109-124, Jul. 1999.
Geng, "Structured-Light 3D Surface Imaging: A Tutorial", Advances in Optics and Photonics, 3:128-160, 2011.
Communication Relating to the Results of the Partial International Search dated May 8, 2014 from the International Searching Authority re: Application No. PCT/IL2013/051059.
International Search Report and Written Opinion dated Sep. 2, 2014 from the International Searching Authority re: Application No. PCT/IL2013/051059.

(56) References Cited

OTHER PUBLICATIONS

International Preliminary Report on Patentability dated Jul. 9, 2015 from the International Bureau of WIPO re: Application No. PCT/IL2013/051059.
International Search Report and Written Opinion dated Apr. 18, 2016 from the International Searching Authority re: Application No. PCT/IL2016/050058.
International Search Report and Written Opinion dated Apr. 21, 2016 from the International Searching Authority re: Application No. PCT/IL2016/050023.
Notice of Allowance and Issue Fee, dated May 12, 2016, for U.S. Appl. No. 14/655,286, filed Jun. 24, 2015.
Notification of Office Action and Search Report dated Jan. 5, 2017 From the State Intellectual Property Office of the People's Republic of China Re. Application No. 201380071840.0 (7 pages).
Notice of Reasons for Rejection dated Feb. 14, 2017 From the Japan Patent Office Re. Application No. 2015-548888 and Its Translation Into English. (10 Pages).
Communication Relating to the Results of the Partial International Search and the Provisional Opinion dated Jun. 14, 2017 From the International Searching Authority Re. Application No. PCT/IL2017/050072. (12 Pages).
Notice of Reasons for Rejection dated Jul. 11, 2017 From the Japan Patent Office Re. Application No. 2015-548888 and its Translation into English (5 Pages).
International Preliminary Report on Patentability dated Jul. 20, 2017 Fmm the International Bureau of WIPO Re. Application No. PCT/IL2016/050023. (10 Pages).
International Preliminary Report on Patentability dated Jul. 27, 2017 From the International Bureau of WIPO Re. Application No. PCT/IL2016/050058. (7 Pages).
International Search Report and the Written Opinion dated Aug. 8, 2017 From the International Searching Authority Re. Application No. PCT/IL2017/050072. (17 Pages).
Communication Pursuant to Article 94(3) EPC dated Aug. 10, 2017 From the European Patent Office Re. Application No. 13830124.7. (6 Pages).
OmniVision "OVM6946 400×400. Compact, Cost-Effective Wafer-Level Camera Module for Single-Use Endoscopes", OmniVision, Product Brief, 2 P., Aug. 10, 2016.
Toshiba "IK-C72: 0.7×0.7 mm, 220×220, CMOS", Toshiba Information Systems, Product Sheet, 1 P., Dec. 2016.
International Preliminary Report on Patentability dated Nov. 16, 2017 From the International Bureau of WIPO Re. Application No. PCT/IL2016/050449. (11 Pages).

\* cited by examiner

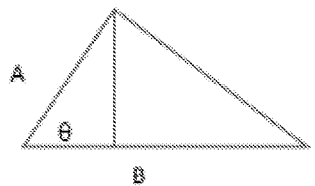
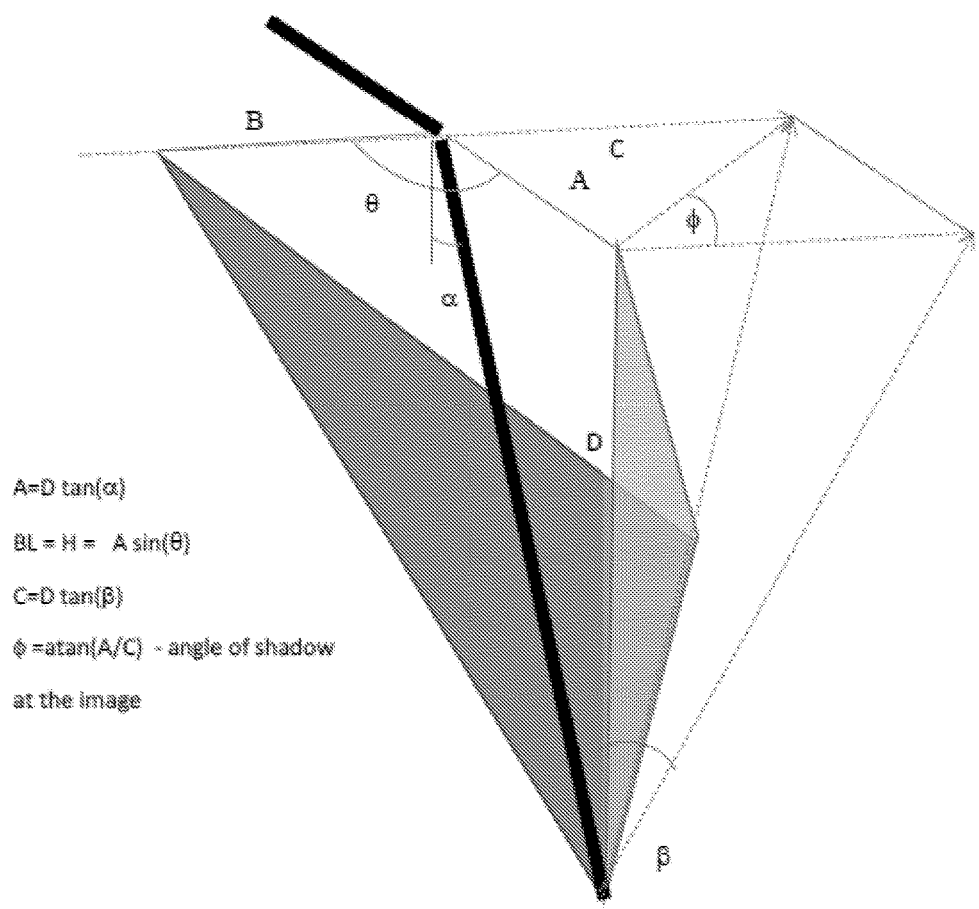
FIG. 1D

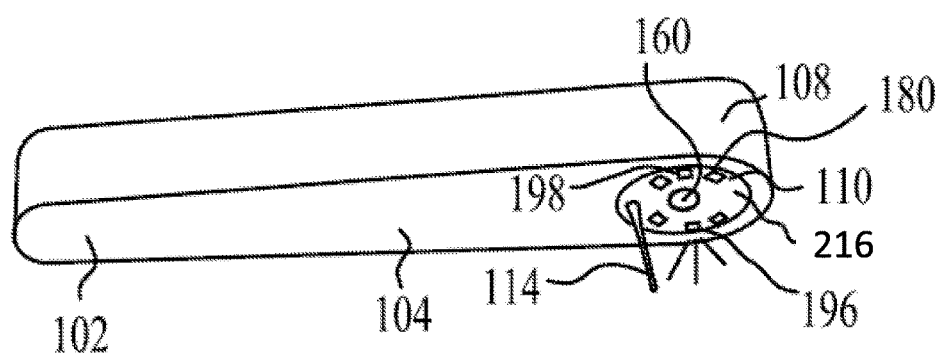
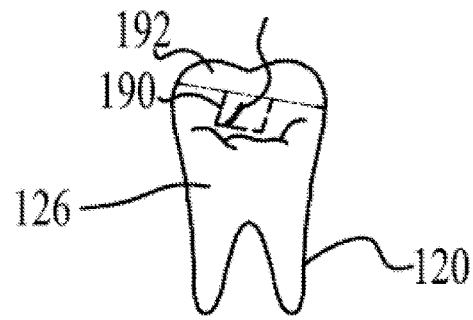
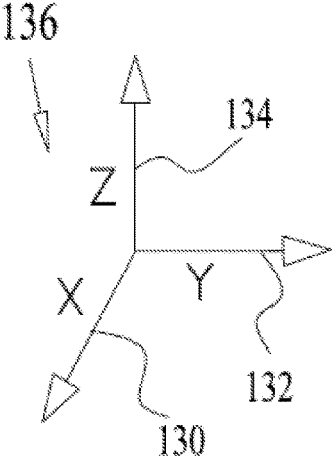
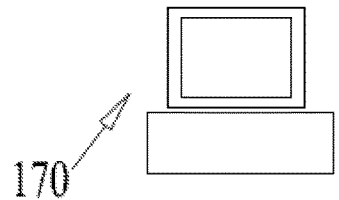
FIG. 2A

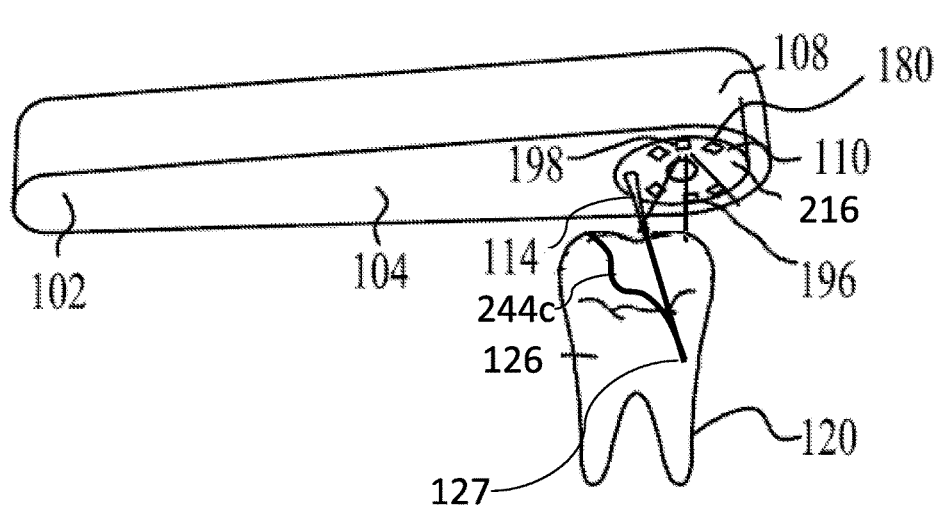
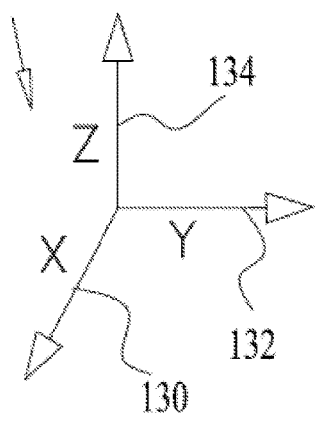
FIG. 2C

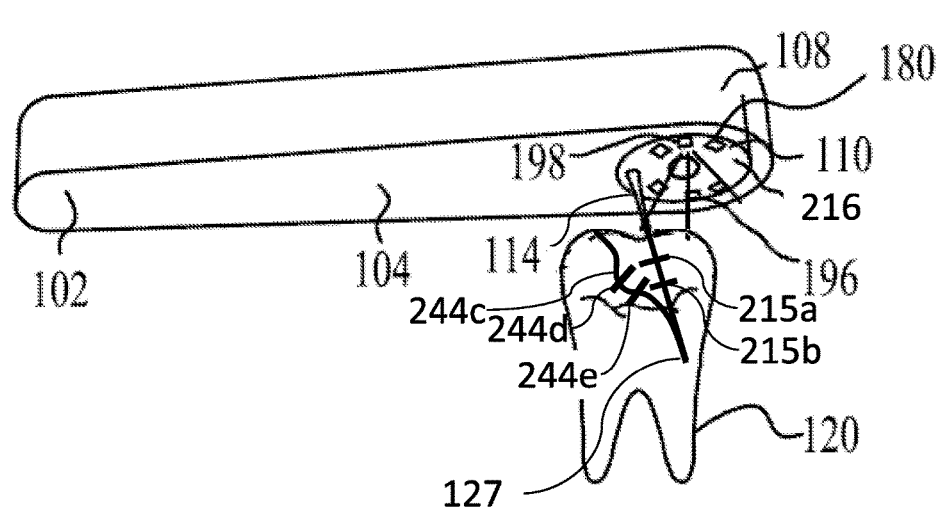
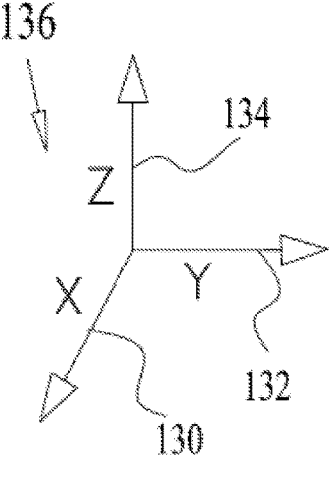
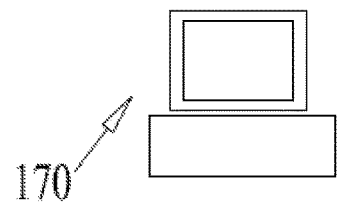
FIG. 2D

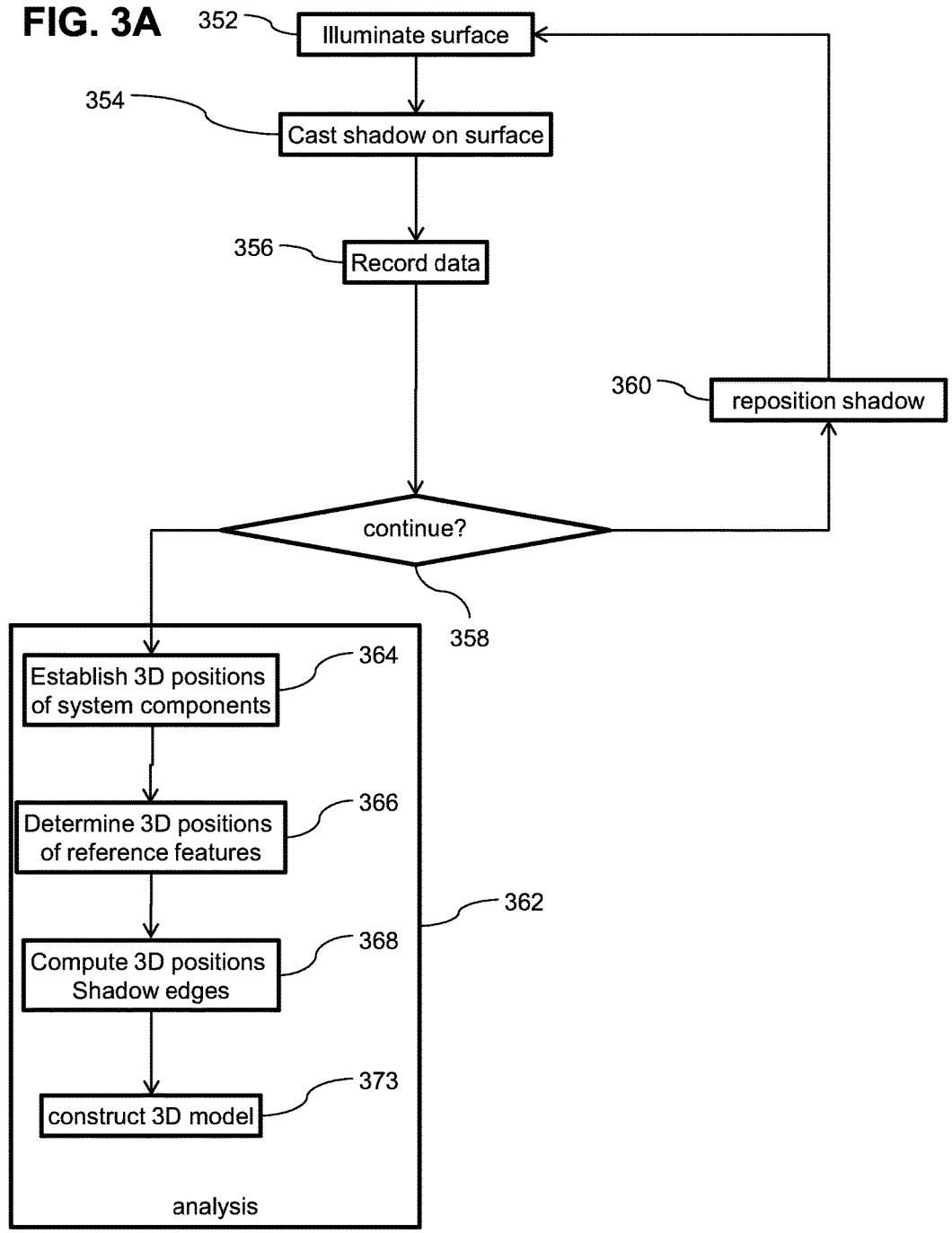

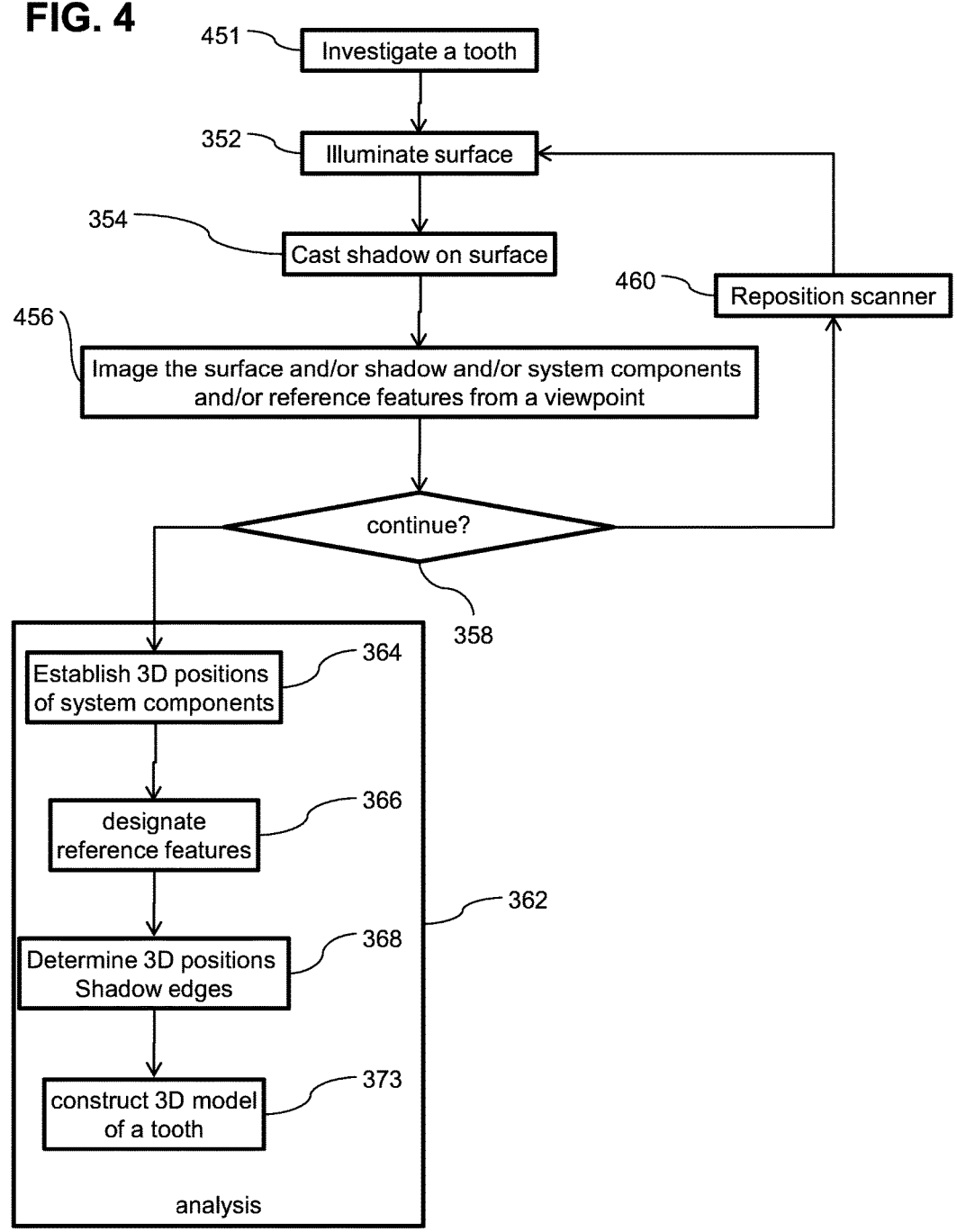

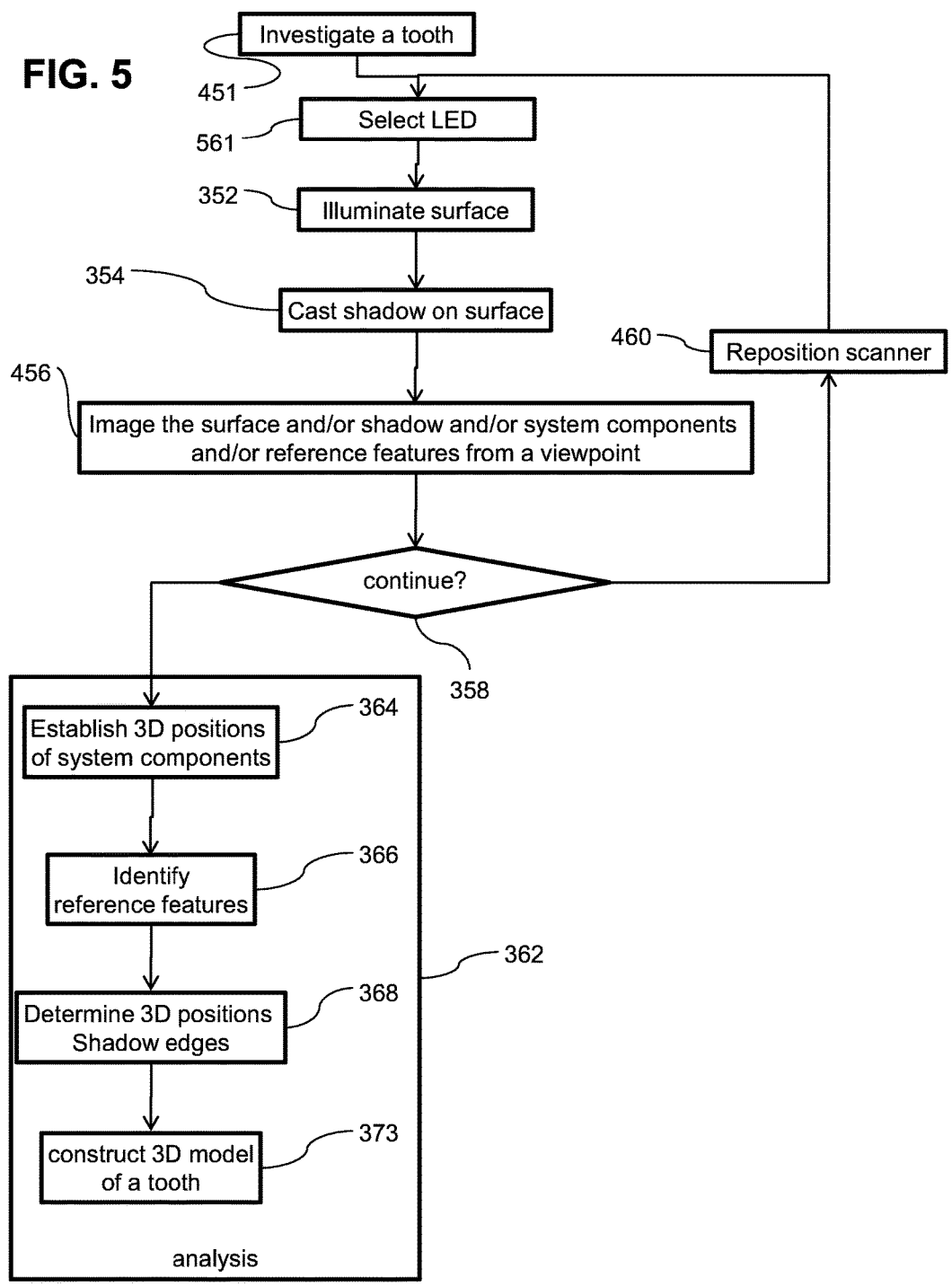

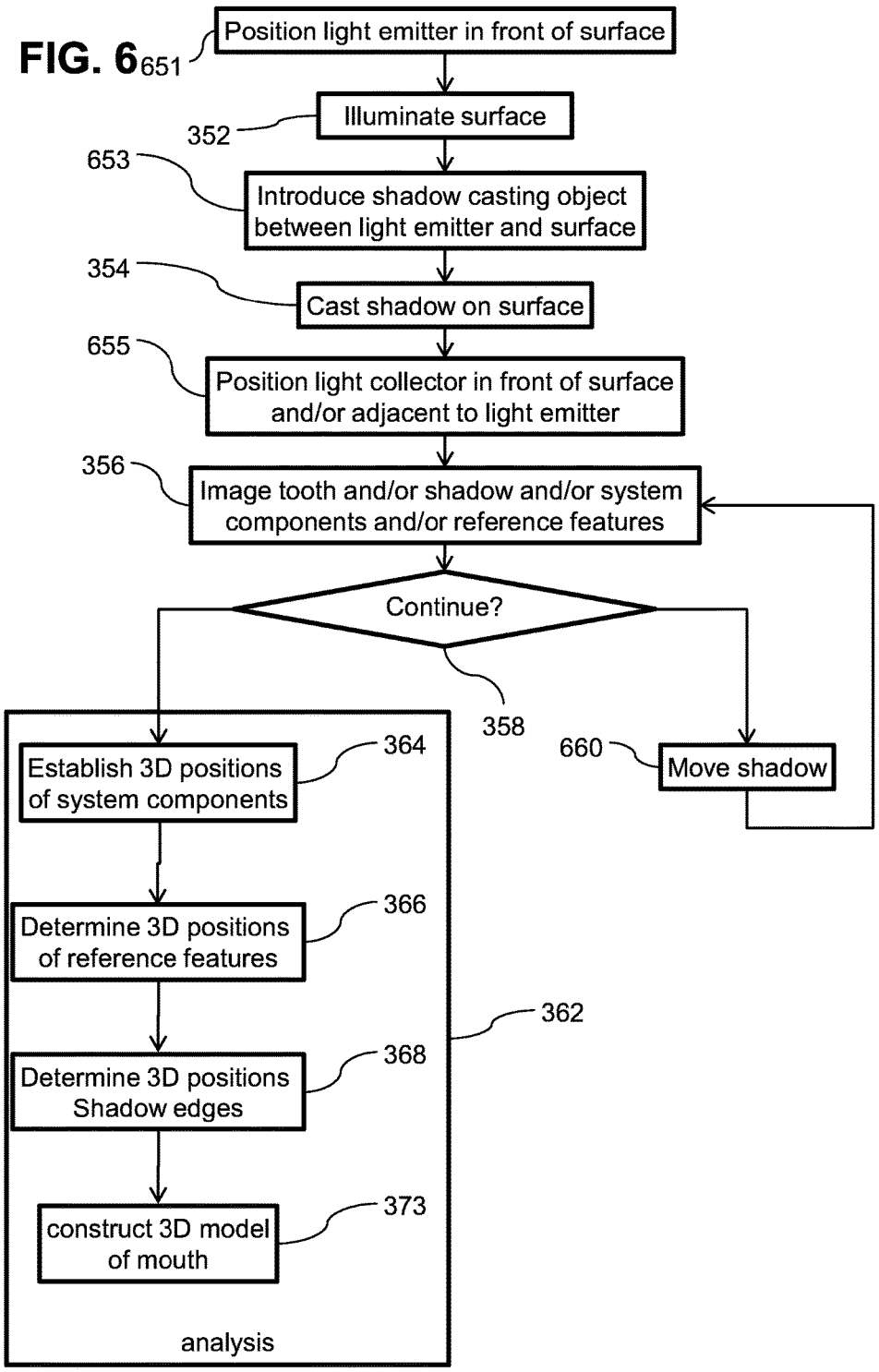

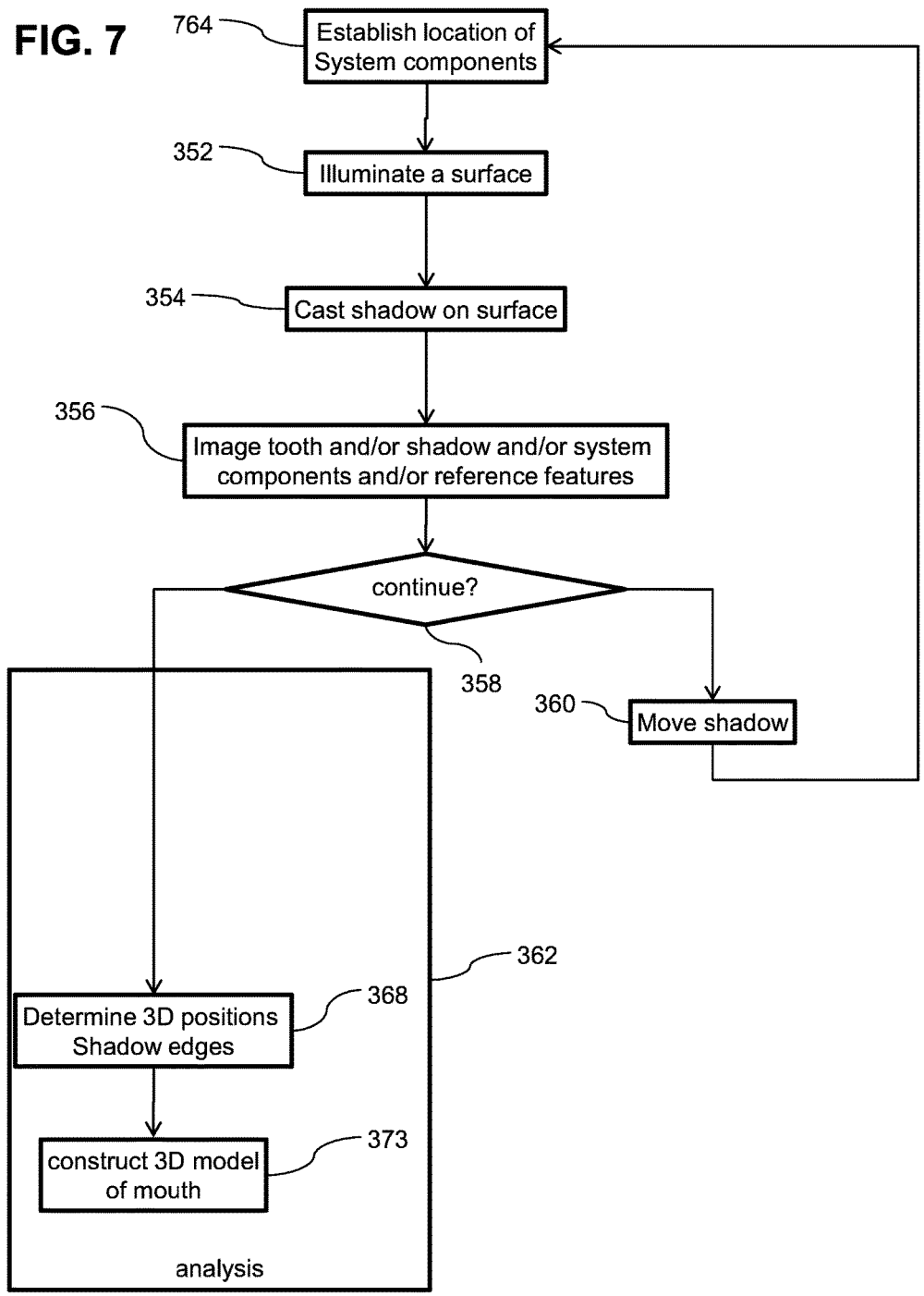

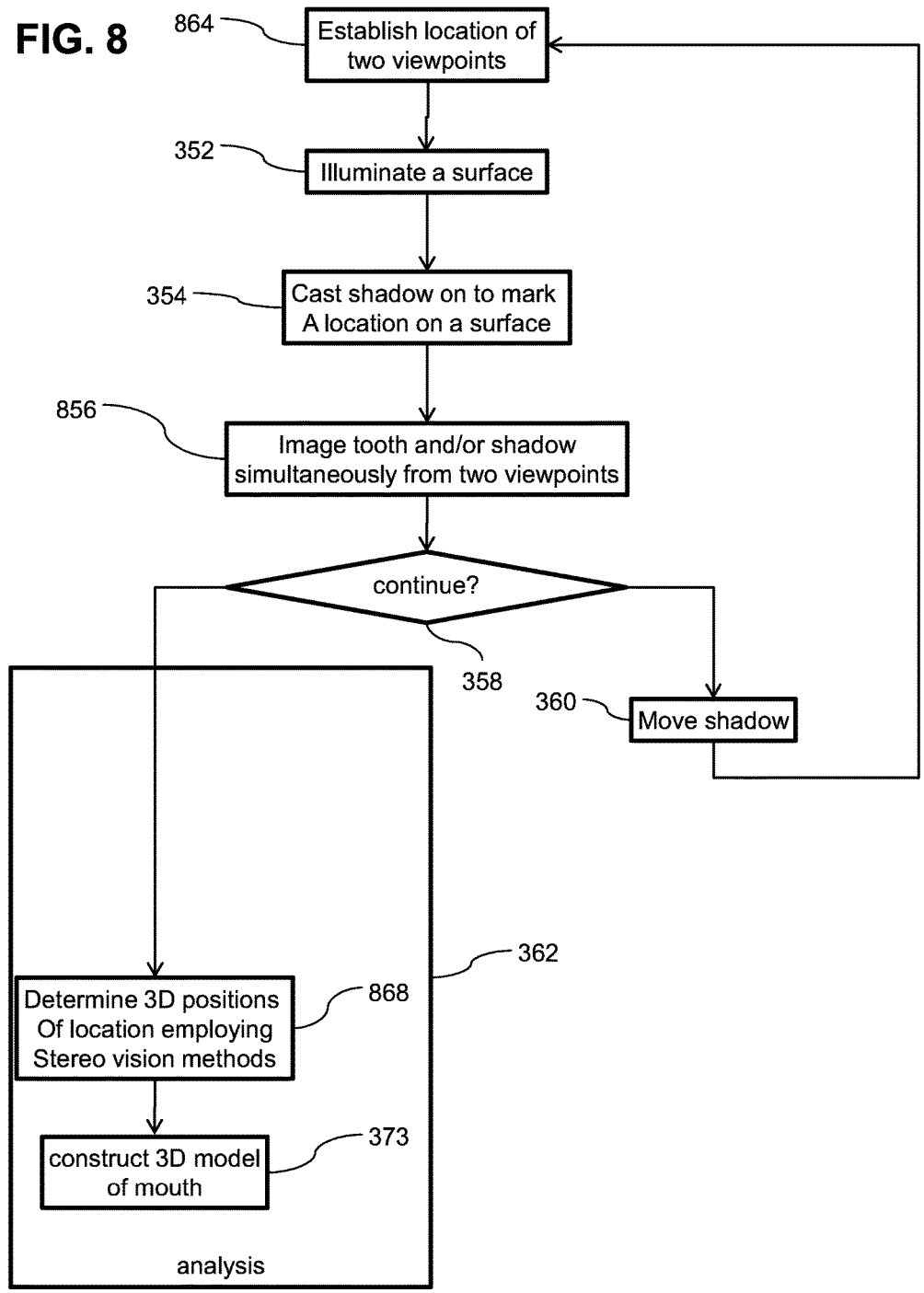

FIG. 9
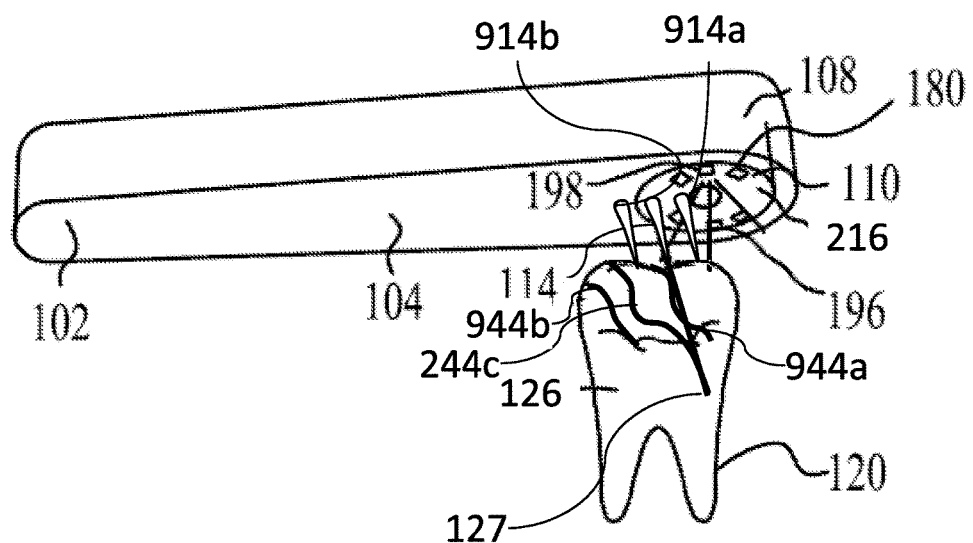
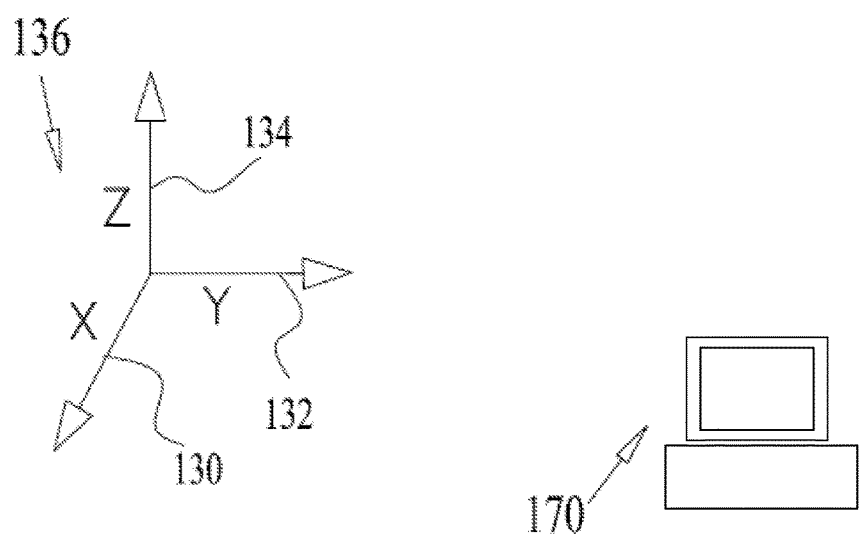

US 10,136,970 B2

SYSTEM, DEVICE, AND METHOD FOR DENTAL INTRAORAL SCANNING

RELATED APPLICATION/S

This application is a National Phase of PCT Patent Application No. PCT/IL2016/050058 having International filing date of Jan. 18, 2016, which claims the benefit of priority under 35 USC § 119(e) of U.S. Provisional Patent Application No. 62/104,835 filed on Jan. 18, 2015. The disclosures of which are incorporated herein by reference in their entirety.

FIELD AND BACKGROUND OF THE INVENTION

The present invention, in some embodiments thereof, relates to a system and method for intra-oral scanning and, more particularly, but not exclusively, to a system and method of determining the geometry of a tooth.

U.S. Published Application 2015/0348320 to the present applicant and others relates to, "A method for measuring regions of a tooth in a mouth including: measuring at least one surface point on a surface of the tooth with respect to an element mechanically coupled to said surface point; determining a location of at least one visible reference mechanically coupled to said surface point with respect to said element; estimating a location of said surface point with respect to said visible reference. A device used for such measuring may include a main body comprising a final optical element of an imager which defines an optical field of view directed in a first direction; and a measurement element coupled to said main body extending generally in said first direction; where a tip of said measurement element is sized and shaped to be inserted between a tooth and adjacent gingiva; where said optical field of view is sized to image at least part of a tooth."

SUMMARY OF THE INVENTION

According to an aspect of some embodiments of the invention, there is provided a method of imaging a tooth comprising: illuminating at least a portion of the tooth with a light emitter; casting a shadow on the portion of the tooth by an object between the emitter and the tooth; imaging the portion of the tooth, including at least a part of the shadow; and determining a location of a point on the tooth and related to the shadow, using the image including the shadow.

According to some embodiments of the invention, the method comprises constructing a shape of the portion based on the determining.

According to some embodiments of the invention, constructing comprises repeating the illuminating, casting, imaging and determining for a plurality of locations.

According to some embodiments of the invention, the method further includes: producing an image of light collected from the portion of the tooth including at least two points related to the shadow; processing the image to determine a 3D location of the at least two points.

According to some embodiments of the invention, the determining comprises determining relative to a model of the tooth.

According to some embodiments of the invention, the determining comprises determining relative to a model of a plurality of teeth.

According to some embodiments of the invention, the method comprises acquiring a plurality of images of the portion and wherein the determining comprises determining a movement of the imager from a plurality of images.

According to some embodiments of the invention, the method further comprises: storing a plurality of the images; designating at least one reference feature in the plurality of images and calculating the location of at least two points related to the shadow with respect to the reference at least one feature.

According to some embodiments of the invention, the reference is at least one of a tooth or gums.

According to some embodiments of the invention, the determining comprises determining a relative position of an imager used for imaging and the tooth and the object.

According to some embodiments of the invention, the object is fixed relative to the imager.

According to some embodiments of the invention, the object is rigid.

According to some embodiments of the invention, the method comprises identifying a deformation of the object.

According to some embodiments of the invention, the method comprises identifying a shape of a portion of the shadow in the image and identifying a point of intersection defined by the shadow and the tooth based on the shape.

According to some embodiments of the invention, the determining comprises determining the location of a line comprising a plurality of points in a same cast shadow.

According to some embodiments of the invention, imaging comprises imaging a plurality of teeth simultaneously with the part of the shadow.

According to some embodiments of the invention, illuminating comprises selecting an illumination point.

According to some embodiments of the invention, illuminating comprises selecting a plurality of illumination points, applied in sequence.

According to some embodiments of the invention, the imaging includes imaging from a viewpoint and wherein determining includes: sighting the point from a viewpoint; and establishing a relative location of the object with respect to the viewpoint and wherein the determining is based on the relative location.

According to some embodiments of the invention, the determining includes: sighting the point from each of two viewpoints; and establishing a relative location of two viewpoints and wherein the determining is based on the relative location.

According to some embodiments of the invention, the method further comprises: inserting an imager into an oral cavity containing the tooth and wherein the determining further includes sighting the tooth with the imager.

According to some embodiments of the invention, the illuminating includes: inserting a light emitter into an oral cavity containing the tooth, and wherein the illuminating is by the light emitter.

According to some embodiments of the invention, the method further comprises: establishing a relative position of the shadow casting object with respect to the light emitter.

According to some embodiments of the invention, the location is with respect to the imager.

According to some embodiments of the invention, the object, an imager used for imaging and a light emitter used for illuminating are fixedly coupled and inserted as a unit into an oral cavity containing the tooth, with the object extending away from a housing of the unit.

According to some embodiments of the invention, the location is with respect to a shadow casting object.

According to some embodiments of the invention, the method comprises storing at most a lower representation of the image after the determining.

According to an aspect of some embodiments of the invention, there is provided a three dimensional (3D) intraoral scanner system for imaging at least a portion of a tooth in an oral cavity comprising: an intraoral portion sized and shaped for insertion into the oral cavity, the intraoral portion including: a light emitter for emitting a light; a shadow casting object; at least a portion of the shadow casting object in a field of illumination of the light source and extending away from a housing of the intraoral portion; an imager positioned to image at least an edge of a shadow cast by the shadow casting object in the light reflected off a portion of a tooth located at a distance of between 3 mm and 5 cm from the imager.

According to some embodiments of the invention, the intraoral scanner system further comprises: a processor configured to process an image of the light received by the imager to provide location information.

According to some embodiments of the invention, the processor is configured to process the image to determine a location of a portion at an edge of the shadow.

According to some embodiments of the invention, the processer is configured to process the image to determine a shape of the tooth.

According to some embodiments of the invention, the processor is further configured to: establish a position of imager with respect to a reference feature in the oral cavity.

According to some embodiments of the invention, the processor is configured to track a position of the portion in the cavity.

According to some embodiments of the invention, the position is provided using the imager.

According to some embodiments of the invention, the processor is configured for the establishing the position of the imager from the image.

According to some embodiments of the invention, the processor is further configured to: establish a position of the object producing the shadow.

According to some embodiments of the invention, the imager is located at a known orientation to the light emitter.

According to some embodiments of the invention, the processor is further configured to: establish a position of the shadow casting object; and establish a relative location of the imager with respect to the light emitter and a portion of the shadow casting object.

According to some embodiments of the invention, a portion of the shadow casting object casting the edge of the shadow has a known orientation to the light emitter.

According to some embodiments of the invention, the processor is further configured to: establish a relative location with respect to the light emitter of a portion of the shadow casting object casting the edge of the shadow.

According to some embodiments of the invention, the system further comprises an elongated handle having a length between 8 to 30 cm, a width less than 15 cm.

According to some embodiments of the invention, the at least a portion of the shadow casting object, the light emitter and the imager are collocated such that they do not fall within 0.5 mm of a single plane.

According to some embodiments of the invention, the system further includes an orientation sensor sensing an orientation of the at least a portion of the shadow casting object with respect to the light emitter.

According to some embodiments of the invention, the orientation sensor includes the imager and wherein the at least a portion of the shadow casting object is within a field of view of the imager.

According to some embodiments of the invention, the emitter radiates light from surface fitting within a sphere of radius 5 mm.

According to some embodiments of the invention, the light emitter comprises a plurality of light sources, not all illuminated at a same time.

According to some embodiments of the invention, the processor is configured for computing a location of at least two spaced apart portions of the shadow with respect to the imager.

According to some embodiments of the invention, the processor is configured to process a plurality of images to designate at least one reference feature in the plurality of images and calculate the location of the at least two portions with respect to the reference feature.

According to some embodiments of the invention, the processor is configured to designate at least 3 features which appear in at least 2 of a plurality of images and calculate the movement of the imager relative of the features.

According to some embodiments of the invention, the processor is further configured to combine location information determined at different imager locations to a single 3D model.

According to some embodiments of the invention, the processor is further configured to combine locations of the at least 3 features identified at different imager locations to the single 3D model that includes the location information determined at each imager location.

According to some embodiments of the invention, the processor is configured to compute a location of at least two points related to the edge of the shadow with respect to an intraoral reference feature.

According to an aspect of some embodiments of the invention, there is provided a system for imaging a tooth in an oral cavity comprising: a light emitter sized and shaped to fit in an oral cavity; an imager sized and shaped to fit in the oral cavity simultaneously with the light emitter and directed to collect light from the light emitter reflected off the tooth at a point of an edge of a shadow on the tooth; a processor configured to receive an image from the imager and process the image to determine a location of the point and a shape of the tooth.

According to some embodiments of the invention, the processor is further configured to: establish a position of imager with respect to a reference feature in the oral cavity.

According to some embodiments of the invention, the processor is configured for the establishing the position of the imager from the image.

According to some embodiments of the invention, the processor is further configured to: establishing a position of the object producing the shadow.

According to some embodiments of the invention, the system comprises: a dental probe sized and shaped so the shadow can be cast by the dental probe.

According to some embodiments of the invention, the light emitter comprises a plurality of light emitter elements and wherein the processor is configured to track the dental probe and to select one or more of the light emitter elements to use for casting a shadow, based on the location of the probe to cast a shadow on the tooth.

According to some embodiments of the invention, the processor is configured to determine a tooth location relative to the dental probe.

According to some embodiments of the invention, the processor is configured to locate an edge of a shadow in an image from the imager and avoid storing a full resolution image thereafter.

According to some embodiments of the invention, the imager comprises two separate and spaced apart imager elements aimed at the point.

According to some embodiments of the invention, a first imager element has a wider FOV (field of view) than a second imager of the imager elements, suitable for imaging an object outside of the tooth, while the second imager element images the point.

According to some embodiments of the invention, the processor is configured to determine a location of the point based on a difference between images acquired by different imager elements.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1D is a simplified schematic illustration of the configurations of the shadow parameter of FIG. 1C;

FIGS. 2A, 2B, 2C and 2D are simplified schematic illustrations of a 3D dental intraoral scanner system with multiple light emitters, according to some embodiments of the present invention;

FIG. 3A illustrates a high level flow chart of an embodiment of a method intra oral scanning using shadows in accordance with an embodiment of the present invention;

FIG. 4 is a flow chart illustration of a method of modeling a tooth while a investigating a tooth with a scanner including a dental probe in accordance with an embodiment of the present invention;

FIG. 5 is a flow chart illustration of a method of modeling a tooth while investigating a tooth with a scanner including a dental probe and multiple light emitters in accordance with an embodiment of the present invention;

FIG. 6 is a flow chart illustration of a semi-passive method of modeling a tooth while a investigating a tooth in accordance with an embodiment of the present invention;

FIG. 7 is a flow chart illustration of a method of modeling a tooth when navigation data is available on the oral cavity in accordance with an embodiment of the present invention;

FIG. 8 is a flow chart illustration of a method of modeling a tooth using multiple overlapping image sensors in accordance with an embodiment of the present invention;

FIG. 9 is a schematic illustration of a scanner having multiple shadow casting objects in accordance with an embodiment of the present invention;

DESCRIPTION OF SPECIFIC EMBODIMENTS OF THE INVENTION

Figure 1A:
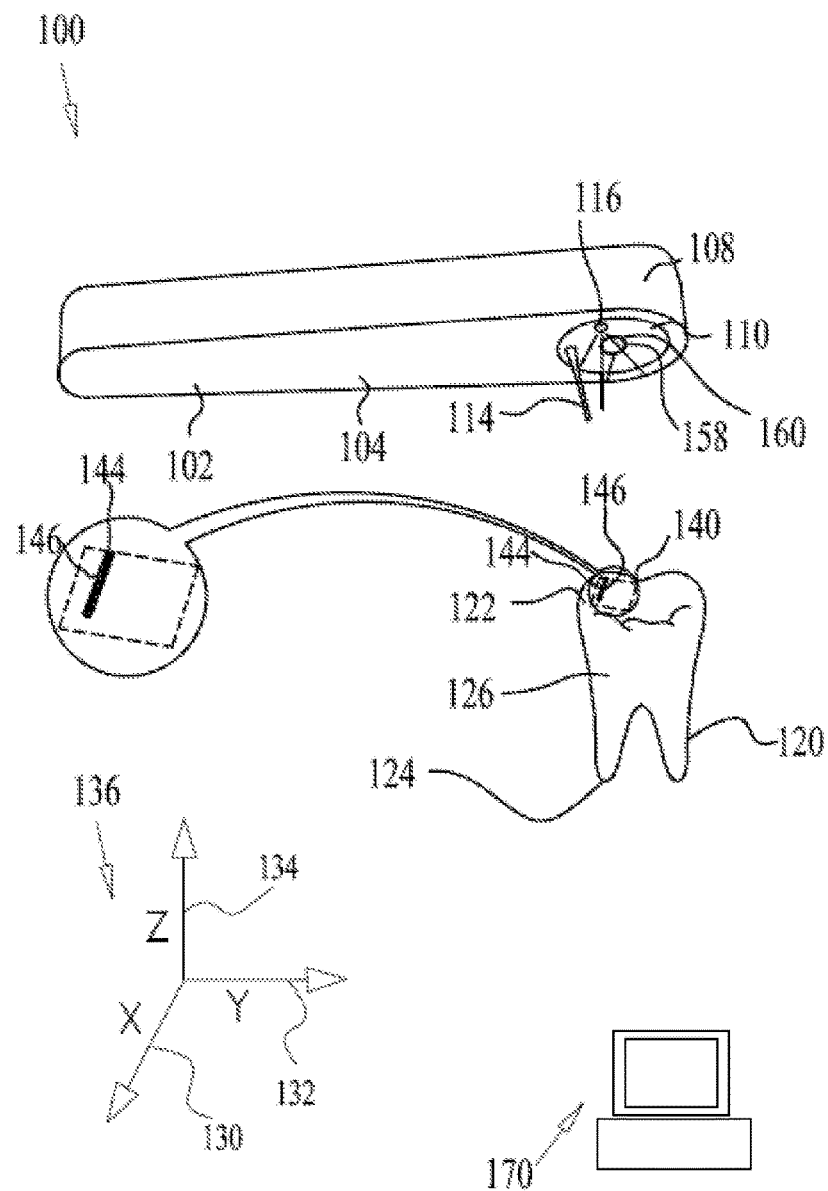
FIGS. 1A and 1B are simplified schematic illustrations of a 3D intraoral scanner system according to some embodiments of the present invention.

The present invention, in some embodiments thereof, relates to a system and method for intra-oral scanning and, more particularly, but not exclusively, to a system and method of constructing a 3D model of a tooth or teeth.

Overview

An aspect of some embodiments of the current invention relates to a method of producing and/or imaging shadows to determine the three dimensional geometry of a tooth surface. Optionally, a shadow may be cast onto the tooth by an object located between the tooth and a light emitter illuminating the surface. In some embodiments, an image of the surface and/or the shadow and/or a portion thereof is captured by a light collector and/or analyzed. A 3D location may be determined of a point related to the shadow (for example a point on the surface at an edge of the shadow and/or one point inside the shadow and one point outside the shadow, delineating the edge of the shadow between the points). Optionally, multiple images may be combined to construct a 3D model of the surface, the tooth, gums, an arch, a portion of the oral cavity and/or the entire oral cavity. Optionally multiple points along a shadow edge will be determined. Multiple points may give information of the size and/or direction of a shadow.

In some embodiments, use of shadows may facilitate measuring and/or determining three dimensional geometry of an intra-oral object (for example a tooth, a bone, and/or an arch). Optionally the imaging is done while simultaneously measuring sub-gingival structures. Optionally measurements are made without the use of penetrating radiation (such as x-ray methods for example tradition x-rays, computerized axial tomography CAT scans, cone beam imaging). Optionally measurements may be made without the use of a laser and/or structured light (for example a projected optical pattern) and/or a computer controlled scanning light emitters. Use of a shadow to discern 3D features has a potential disadvantage that shadow edges may tend to get fuzzy and/or diffused and/or spread as the distance increases between the shadow producing object and the surface upon which the shadow falls. Nevertheless, in some embodiments, a device producing shadows may be cheaper and/or smaller than a device producing a projected grid etc.

In some embodiments, the location of a point on a shadow may be calculated, for example as the intersection of two lines. For example, the two lines may include two lines of sight from two spaced apart view points to the point on the shadow. For the sake of this disclosure a view point may be the location of a light collector, for example the centroid of the optical aperture thereof, for example a camera and/or another imager. For the sake of this disclosure a line of sight may includes the line from the view point to the point being measured (e.g. the edge of the shadow on the surface and/or the centroid of an area, for example a blurred edge). For example, the coordinates of the point being measured may be found using in stereo vision methods for example including binocular range finding where the location is at the intersection of the two lines of sight from two spaced apart view points to the point being measured on the surface. Alternatively or additionally, the location of a point on a shadow on the surface may be identified as the intersection of a line of sight and a line of illumination. For the sake of this disclosure, a line of illumination may include a line from an illumination point and/or a centroid of a light emitter to the location being measured, for example the centroid thereof. For example, a line of illumination to a point on the edge of a shadow includes a line passing from the illumination point, past the edge of the shadow producing object to the edge of the shadow on the surface. Alternatively or additionally, for example, when a shadow is cast by an object with a straight edge, all the points of the shadow edge may fall in a plane defined by the illumination point and the line of the edge of the shadow casting object. In some embodiments, the 3D location of a point on the tooth may be determined by computing the point of intersection between the plane of the shadow edge and the line of sight from the imager to the point. The direction of the line of sight to the point is optionally calculated from the location of the point in an image. The plane of the shadow is optionally determined by the location of the light emitter aperture and the edge of the shadow casting object.

In some embodiments, the illuminated portion of a shadow producing object may have a short dimension of between 0.1 to 0.3 mm and/or between 0.3 to 0.7 mm and/or between 0.7 to 3 mm and/or between 3 to 10 mm and/or between 10 to 30 mm. Optionally the illuminated portion of a shadow producing object may have a long dimension of between 0.1 to 0.3 mm and/or between 0.3 to 0.7 mm and/or between 0.7 to 3 mm and/or between 3 to 10 mm and/or between 10 to 30 mm and/or between 30 to 50 mm or more. For example the shadow casting object may be elongate with a long illuminated dimension between 3 to 5 times the short illuminated dimension and/or between 5 to 10 times and/or between 10 to 50 times or more.

In some embodiments, the area of a shadow on an image may be less than $1/100$ the illuminated area and/or between $1/100$ to $1/20$ of the illuminated area and/or between $1/20$ to $1/10$ of the illuminated area and/or between $1/10$ to $1/4$ of the illuminated area and/or between $1/4$ to $1/2$ of the illuminated area and/or between 1/1 to equal to the illuminated area and/or between equal to twice the illuminated area and/or between twice to four times the illuminated area and/or between four times to ten times the illuminated area and/or between ten times to one hundred times the illuminated area. In some embodiments, an image may include less than 100 shadow edges and/or less than 10 shadow edges and/or less than 5 shadow edges and/or less than 3 shadow edges. In some embodiments, an image may include less than 100 parallel shadow edges and/or less than 10 parallel shadow edges and/or less than 5 parallel shadow edges and/or less than 3 parallel shadow edges. In some embodiments, the total length of shadow edges in an image may be less than 100 times the length of the long edge of the image and/or between 10 to 100 times the length of the long edge of the images and/or between 1 to 10 times the length of the long side of the images and/or between $1/4$ to 1 times the length of the long side of the image and/or less than $1/4$ the length of the long edge.

In some embodiments, a shadow will be in the central portion of an image. For example the shadow may fall entirely in the central (from side to side and/or from top to bottom) $1/2$ of the image and or the central $1/4$ of the image. Alternatively or additionally, the shadow may fall entirely in the peripheral (from side to side and/or from top to bottom) $1/2$ of the image and or the peripheral $1/4$ of the image. In some embodiments, a shadow may have one outer edge inside an image and/or between 1 to 4 outer edges in the image. In some embodiments, a shadow in an image may include a projection of an outer edge of the shadow producing object and/or of two opposing edges of the shadow may be projections of two opposing outer edges of the shadow producing object.

In some embodiments, the distance of the shadow producing objects to the surface being imaged may be less than 1 mm and/or between 1 mm to 3 mm and/or between 3 mm to 10 mm. In some embodiments, the distance of the shadow producing objects to the surface being imaged may be less than 1 mm and/or between 1 mm to 3 mm and/or between 3 mm to 10 mm. In some embodiments, the distance of the light emitter to the surface being imaged may be less than 1 mm and/or between 1 mm to 3 mm and/or between 3 mm to 10 mm.

In some embodiments, a feature in a shadow may be used to mark a point on a surface (for example the surface may lack identifiable features e.g. a smooth surface). For example, the location of the marked point may be imaged from two view points and its location found by triangulation (for example stereoscopy or using at least 2 images made at spaced apart viewpoints, the images are optionally made by a single camera and/or using multiple cameras and/or a camera with multiple apertures). Alternatively or additionally, a shape of a shadow may be used to determine a shape of a surface. For example, a bending of a shadow may indicate that a surface is bent and/or lengthening of a shadow may indicate that a surface is angled away from the light emitter and/or an axis of the shadow producing object. Optionally, a cast shadow may be used for discovering object's concavities, which are sometimes difficult to measure based on other cues such as occluding boundaries.

Optionally some or all of the light collector, light emitter and/or shadow producing object have a fixed relative location. For example, they may be fixed in an intraoral scanning device. Alternatively or additionally, the field of view FOV of the light collector may include at least a portion of the shadow casting object such that the location of the shadow casting object and/or deformation of the shadow casting object may be identified by image analysis. The location in 3D space of a point related to the shadow may be adjusted using image of said shadow casting object. Optionally the location of the light collector may be identified with respect to features in an oral cavity by image analysis.

In some embodiments, an imaging method may include establishing a spatial relationship between components of the system. For example, a spatial relationship may be tracked in real time. For example, relative positions may be tracked using an optical tracking system, for example one or more cameras sighting a system component and/or the oral cavity. Alternatively or addition, a location of a component may be tracked using a beacon (for example a radio frequency RF beacon) and/or a local positioning system. Alternatively or additionally, some aspects of a spatial relationship between components of the system may be fixed.

In some embodiments, light emitter may include any object that illuminates the tooth. For example, the light emitter may include a light source such as a light emitting diode and/or a laser. Alternatively or additionally, the light emitter may include a light shaping element such as a lens and/or an optical fiber.

In some embodiments, an object may be actively introduced between a light emitter and a tooth to produce the shadow. Alternatively or additionally, a shadow may be produced by the geometry of the tooth itself and/or by a passive object. For example, the shadow casting object may include a dental tool and/or a specially designed probe with optional fiducial marking.

In some embodiments, measurements of the shadow edge 3D profile may have a tolerance of, for example, between 10 um to 50 um and/or between 50 um to 100 um and/or from 100 um to 200 um.

In some embodiments, relative position of system components may be established to a linear tolerance, of for example, between 10 um to 50 um and/or between 50 um to 100 um and/or from 100 um to 200 um. Optionally an imaging sensor may have a resolution of about 1 Mpixels. For example, the resolution may vary over a range, for example, of 0.4-15 Mpixels or even lower or higher resolutions. Optionally a light collector may have a FOV of about 60 deg. For example the FOV may vary over a range of for example 10 to 30 degrees and/or 30 to 60 degrees and/or 60 to 90 degrees or greater or smaller.

In some embodiments, imaging a shadow may result in measurements and/or images that will be used to establish a spatial relation during post processing. For example, images produced by a light collector may be analyzed to establish a spatial relationship. Optionally the light collector may have a field of view FOV that includes a shadow producing object and/or a light emitter. Optionally an imaged produced from the light collector may be analyzed to establish a position of the shadow producing object and/or a navigational reference feature with respect to the light collector. Alternately or additionally a fiducial marker may be used and/or a position sensor. Data from the marker and/or the position sensor may be processed to establish the location of one or more components of the system.

In some embodiments measuring an oral cavity and/or intra-oral object may include establishing a spatial location of components of the system and/or of determining a spatial location of an image feature with respect to a reference feature, for example an intra-oral object and/or feature. Except where clearly used otherwise, the term navigation is used in this disclosure to mean establishing the location of a system component with respect to a reference (for example a reference feature in the oral cavity). For example, a location may be tracked in real time. Optionally, the location may be tracked based using an optical tracking system, for example one or more cameras viewing a system component and/or the oral cavity. Alternatively or additionally, a location of a system component and/or an imaged object and/or a reference feature may be tracked using a marker and/or a beacon (for example a radio frequency RF beacon) and/or a local positioning system signal.

In some embodiments, a previously identified reference feature (for example an object identified in a previous intra-oral scan and/or in a CT scan) may be used to as references to establish the location of a system component and/or determine the location of an imaged object. Alternatively or addition, reference features may be recognized during processing of a collection of data. In some embodiments artificial reference markers may be used, for example marking a location on a tooth with a dye and/or powder and/or a sticker and/or placing a fiduciary marking in the oral cavity. In some embodiments, natural reference features may be used, for example a distinguishable feature of a tooth and/or a pallet and/or an arch. In some embodiments, a fixed dental structure may be used as a reference, for example a crown and/or a bridge. Alternatively or additionally, inertial navigation may be employed to track the location of a system component and/or an object in the oral cavity. For example, a gyro and/or an accelerometer may be attached to a component of the system and/or an object in the oral cavity.

In some embodiments, images may be made simultaneously or nearly simultaneously. For example, an imagers may capture a pair of images in less than one second (sec) and/or between 1 to $\frac{1}{30}$ sec and/or between $\frac{1}{30}$ to $\frac{1}{200}$ sec and/or between $\frac{1}{200}$ to $\frac{1}{700}$ sec and/or between $\frac{1}{700}$ to $\frac{1}{1000}$ sec. Optionally the capture rate may be even higher for lower resolution and/or smaller ROIs. For example, separate images may be captured with a light emitter activated in a different position resulting in a different position of a shadow. Alternatively or additionally multiple light collectors may be illuminate the imaged structure from different locations. The different light emitters may have different frequencies and/or be activated in quick succession to produce shadows at multiple locations substantially simultaneously. For the sake of this disclosure substantially simultaneously may mean within a time period wherein the oral cavity normally moves less than a measurement tolerance. For images made substantially simultaneously, the spatial relationship between locations may be determined from their relative spatial positions.

An aspect of some embodiments of the current invention relates to intra-oral scanning device. Optionally, the device includes one or more light collectors and/or one or more light emitters and/or one or more shadow producing elements (for example a dental tool). Optionally the scanning device may include a housing (for example components such as the light emitter, image and/or shadow caster may be mounted to the housing and/or may be contained in the housing and/or may be integral to the housing). Optionally the relative orientation of the components in the housing is known and/or fixed. Optionally one or more of the system components is included in a portion of the housing shaped and sized to fit into an oral cavity. Optionally the housing is shaped, sized to be handled by a single human hand from outside the oral cavity. For example, a user may use a handle outside the oral cavity to manipulate the scanner inside the cavity.

In some embodiments, a spatial relationship may be established based on a fixed spatial relationship between some elements of the system. For example, a light emitter and a light collector may be fixed in a tool with a fixed geometric structure. Alternatively or additionally, a shadow producing object such as a probe may be fixed in the tool. Alternatively, a light collector and a shadow producing object may be fixed into a tool. Alternatively, a light emitter and a shadow producing object may be fixed into a tool. Alternatively or additionally one or more light emitters and/or light collectors may be independent of the tool. Alternatively or additionally there may be multiple tools including one or more of a light emitter, a light collector and/or a shadow producing object.

In some embodiments, a light collector may include an image sensor and/or a light shaping element (for example a lens and/or optical fiber) directing light to an image sensor. An example of an image sensor is for instance a CMOS sensor [for example an ON-Semi Python1300 CMOS sensor available from ON Semiconductor 5005 East McDowell Road Phoenix, Ariz. 85008 USA, with 1.3 Mpixels (1024× 1280) resolution, global shutter to avoid image distortions because of movements, that captures up to 545 frames per second FPS on full frame and 1000s FPS on smaller ROIs. Optionally a sensor may have between 10 to $10^3$ pixels and/or from $10^3$ to $10^5$ pixels and/or $10^5$ to $5 \times 10^5$ pixels and/or $5 \times 10^5$ to $5 \times 10^6$ pixels and/or $5 \times 10^6$ to $5 \times 10^7$ pixels and/or $5 \times 10^7$ to $10^9$ pixels.

In some embodiments, a light emitter may include a light emitting element and/or a light shaping element (for example an optical fiber and/or a lens) directing light to a region of interest ROI (for example an intra-oral object including a tooth and/or a reference feature and/or a shadow producing object for example a dental tool). For example, a white LED may be used. In some embodiments, white illumination facilitates obtaining a color image of the ROI. For example the light emitters may be point emitters of light for example having a light emitting surface of between 3 to 1 $mm^2$ and/or between 1 to $\frac{1}{10}$ $mm^2$ and/or between $\frac{1}{10}$ to $\frac{1}{100}$ $mm^2$ and/or between $\frac{1}{100}$ to $\frac{1}{10000}$ $mm^2$. For example, a larger light emitter may include an LED and/or a smaller light emitter may include a laser diode. For example, where the light emitter is large, the distance between the shadow producing object and a surface being imaged may be decreased and/or where the light emitter is large, the distance between the light emitter a surface being imaged may be increased.

In some embodiments, a housing may have a length ranging between 10-25 cm. In some embodiments, a housing may have a maximum width ranging between 1-3 cm. In some embodiments, a system may have a weight ranging between 20 g-1 Kg.

In some embodiments, the shadow producing element may include a dental tool, for example, a periodontal probe. For example, the tool may protrude to a distance between 5-25 mm from the housing. For example, the tool may have a maximum width ranging between 1-3 mm. For example, the tool may include a fiducial marking. For example, fiducial markings may include a protrusion, a small ball, a hole, a colored area and/or an indentation. Optionally, markings may be arranged to indicate an orientation, for example an angle and/or a length. In some embodiments, the distance between a light emitter and a light collector may range between 1 to 10 mm and/or between 10 to 50 mm and/or greater than 50 mm. In some embodiments, a distance between a light emitter and a probe tip may range between 5-50 mm or more than 50 mm. In some embodiments, the distance between a light collector and a probe tip may range between 5-50 mm or more than 50 mm. In some embodiments, a probe may have a sharp tip.

In some embodiments, a navigation sensor may be provided. For example, a tool may include a light collector for imaging a tooth and/or a shadow producing object and/or a navigation sensor, which is used to establish the location of the light collector. For example, the navigation sensor may include an imaging light collector whose orientation to a light emitter, light collector and/or shadow casting object is fixed. The navigation sensor is optionally configured to detect its location with respect to a reference feature and/or the navigation sensor optionally has a wide field of view for capturing an orientation to a reference feature. Alternatively or additionally a single light collector used for locating a point on a shadow and/or navigating, for example the light collector may have a wide FOV to capture the reference features along with the shadow. Optionally the FOV may be between 5 to 25 degrees and/or between 25 to 45 degrees and/or between 45 to 90 deg and or greater than 90 degrees. Reference features in the FOV of the light collector may optionally be used for navigation.

An aspect of some embodiments of the current invention relates to intra-oral scanning and/or navigation during use of a dental tool (for example a probe used to measure a sub-gingival feature or a dental drill). For example, images may be recorded of a dental probe, a revealed surface of a tooth and/or gums, a reference feature and/or a shadow on the surface. The images may be processed in real time and/or in post processing to establish the location of the probe in relation to the reference feature and/or the geometry of the surface and/or the orientation of geometric features of the surface with respect to the reference feature. Optionally image recording may be accomplished with minimal or no interruption of the use of the probe.

In some embodiments, while a user measures teeth or gums of a subject using a dental probe, images may be collected showing the probe position and/or a shadow of the probe on a tooth and/or shadows of shadows cast by tooth structures. The images may be later processed to produce a model of geometry of the tooth and/or determine locations of measurements made with the probe. For example, a portion of the shadow casting object may be distanced from the light source between 0.1 to 1 mm and/or between 1 mm to 5 mm and/or between 5 mm to 30 mm and/or between 30 mm to 50 mm and/or greater than 50 mm. For example, the shadow casting object may move independently of the probe.

In some embodiments, the device may measure deformations of the probe. For example, deformation of the probe may be used to determine when and/or where the probe tip contacts a sub-gingival object. Alternatively or additionally, a calculation of shadow location may be corrected for deformations of the shadow casting object.

In some embodiments, a light emitter may be configured to reduce interference with activity of the user. For example, while a user is measuring teeth and/or sub-gingival structures under visible light (for example wide bandwidth white light), light emitters and/or collectors may be illuminating and/or imaging structures using non-visible wavelengths (e.g. UV and/or IR). Alternatively or additionally, while a user is measuring teeth and/or sub-gingival structures under visible light (for example wide bandwidth white light), light emitters and/or collectors may be illuminating and/or imaging structures using visible light in a narrow bandwidth.

An aspect of some embodiments of the current invention relates to a method and system to track shadow casting object in real time and direct a device for imaging a shadow of the object on a tooth. In some embodiments, a processor may be configured to track the shadow casting object. The processor may optionally, direct a select a light emitter for activation and/or direct a light emitter in order to cast a shadow of the object on the tooth. Alternatively or additionally, a system for mapping an oral cavity may track movement of a shadow casting object and direct a light collector towards the location of the shadow. Alternatively or additionally, the processor may track a position of a tooth and a light source and position the shadow casting object to cast a shadow on the tooth. In some embodiments the location of features and/or shadows are located in a model and/or in the coordinate system of a model. Optionally features of the model may be constructed using interpolation and/or extrapolation. Optionally measured features will be related to the model.

In some embodiments, an intra-oral scanning system may include multiple light sources and/or one or more shadow casting object. A dental system may include a processor that tracks the orientation of the light sources and/or shadow casting objects and selectively activates a light source in order to cast a shadow on a particular tooth and/or a particular region of a tooth.

In some embodiments, the processor identifies the location of a scanned tooth in an image captured by an imager. For instance, the tooth may be identified relative to the gums using color segmentation. The processor optionally uses the tooth location relative to the probe to illuminate the probe with at least one light source to cast a shadow on a ROI on the tooth. For example, while the probe scans the tooth, different light sources are selected to illuminate the ROI and cast the shadow at a desired location. Factors considered in selecting the light source may include, for instance the contrast between the shaded and illuminated regions, and/or measurement error at different regions (for example a shadow may be projected where it has the largest baseline related to the imager).

In some embodiments, the image of the cast shadow and/or may be analyze a cast shadow to decide which light source to activate.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

DETAILED EMBODIMENTS

Intraoral Scanner with a Single Light Source

Figure 1B:
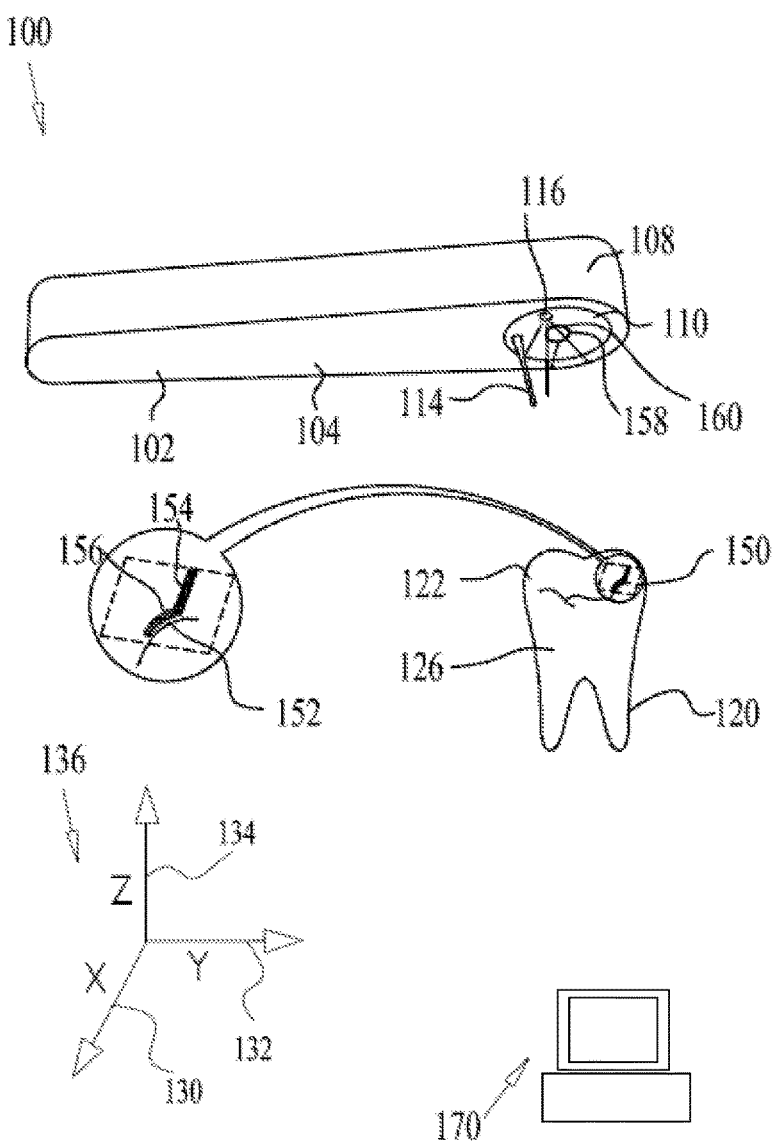

Referring now to the figures, FIGS. 1A and 1B are each a simplified schematic illustration of a 3D dental intraoral scanner (IOS) system 100 according to some embodiments of the present disclosure. As seen in FIGS. 1A-D, the exemplary IOS system 100 comprises an IOS 102. IOS 102 includes a hand piece 104 and a head portion 108. In accordance with some embodiments, from an oral-facing surface 110 of the head portion 108 extends a shadow casting object 114 (shadow casting object is an object located between a light emitter and the tooth, such that a portion of said shadow casting object casts a shadow on at least a portion of the tooth. In some cases said shadow casting object may have also a dental functionality, for example a dental probe, or ultrasonic scaler, or a dental drill or dental turbine or any other dental tool.) In the schematic embodiment shown at FIGS. 1A-D, shadow casting object 114 is a dental probe. The oral-facing surface 110 optionally includes a light emitter, light source 116, and an optical aperture 158 of a light collector, camera 160.

In some embodiments light source 116 may include any suitable light source, such as a light-emitting diode (LED), a laser, such as edge emitter or VCSEL etc. Light source 116 optionally includes beam shaping optics, such as a lens, for example to use the light source light efficiently. The light source spectrum may be for instance blue, such as 450 nm LEDs or lasers, which may in some embodiments provide better contrast on the tooth or any other spectra, such as white or green or IR light etc. In some embodiments, optical fibers with a remote light source may be used.

In some embodiments, probe 114 and/or light source 116 may be utilized for 3D measurements of a portion of a tooth 120, and/or for measurement of the full tooth and/or for measurement of a plurality of teeth and/or for measurement of a partial or full dental arch and/or at least a portion of the dental arch.

In some embodiments, during scanning, light source 116 may be illuminated onto a chosen surface, for example to illuminate surface of a tooth or gums. The illumination is optionally used for imaging the surface. The chosen surface may comprise any surface on the tooth, such as a top surface 122, a bottom surface 124 and/or side surfaces 126 thereof.

In some embodiments, the illumination also falls on probe 114. Optionally, probe 114 casts a shadow on a chosen surface 140 of a tooth 120 or gums. The shadow may include a projection of the probe geometry on the chosen surface. The tooth image is optionally captured by a light collector, for example camera 160 through an optical aperture 158. Optionally, a portion of probe 114 is seen in the camera image as well as a portion of its shadow 144 (for example as illustrated in FIG. 1A) on a tooth surface 140.

Figure 1C:
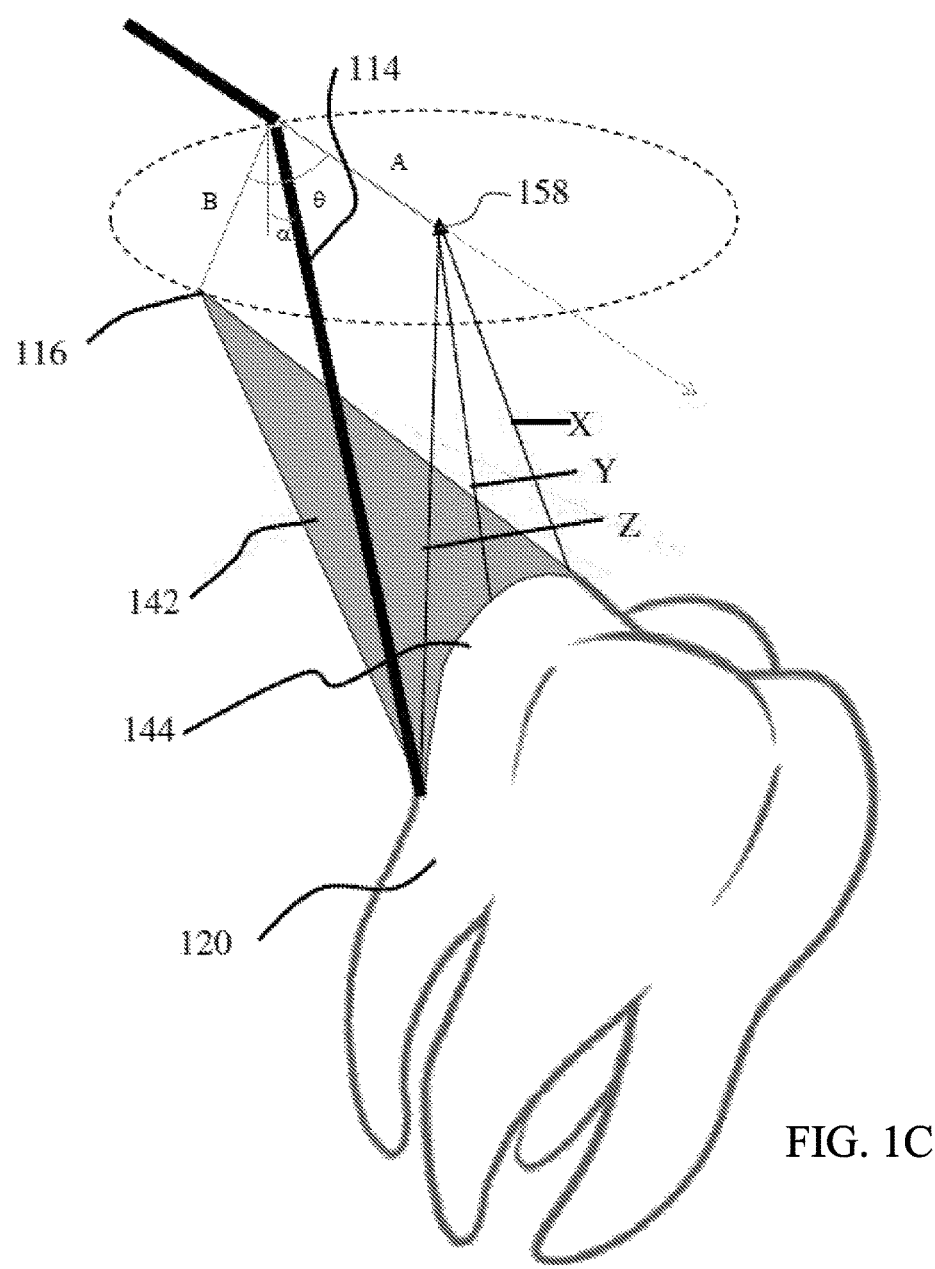
FIG. 1C is a simplified illustration of a 3D intraoral scanner system according to some embodiments of the present invention.

In some embodiments probe 114 has a linear edge. Optionally, the projection of the linear edge of the probe shadow 144 may be geometrically considered as included in a plane 142 (for example as illustrated in FIG. 1C) defined by the respective probe edge and light source 116. Each point in the shadow edge image falls somewhere in plane 142. The line of sight from optical aperture 158 to a point on the shadow defines a ray such as rays X, Y and Z that extends from optical aperture 158 to plane 142. The point of intersection of the ray and the plane is also the edge of the shadow on the surface. In some embodiments, the 3D location of the intersection of a ray and a plane is calculated. The intersection may optionally provide a 3D profile of a tooth portion. In some embodiments, to get 3D information, optical aperture 158 is located outside of the plane of light emitter 116 and probe 114.

In some embodiments, features and/or the shape of a surface is understood from the shape of a shadow on the surface. For example, the intersection between plane 142 and a flat surface would be a line. Curves bends or deformations of the line of the shadow indicate a curvature or deformation and/or angling of the surface.

In some embodiments shadow 144 forms a 3D line on surface 140. The line is optionally imaged by camera 160. In some embodiments, the orientation of a ray (for example rays X, Y, Z) between the camera and the shadow are derived from the image made by the camera. The 3D orientation of the ray may be found from the image, for example using the camera intrinsic and extrinsic parameters, such as the angle of the camera and the camera optics. Alternatively or additionally, the 3D orientation of the ray may be found, for example by relating the position of the point of the shadow in the image to the position of one or more reference features in the image. The 3D relationship between light source 116 and probe 114 are optionally used to calculate the orientation of plane 142. For example, based on the orientation of plane 142 and the orientation of a ray to a point on shadow 144 (for example rays X, Y and Z) the location of a point on shadow 144 is determined in any coordinate system, for example the system defined by an X axis 130, a Y axis 132 and a Z axis 134 relative to the IOS 102. A non-limiting example of a configuration of the shadow parameters, such as the angle and length are shown in FIG. 1D, which is self explanatory.

In some embodiments, the 3D coordinates of shadow 144 obtained in an image are stored in a coordinate system related to the position of the IOS at the time that the image was made, this coordinate system may be referred to as an IOS coordinate system. Optionally, the IOS coordinates system of different images may differ, for example due to movement of camera between images. In some embodiments, the IOS coordinates of shadow 144 are transformed into a tooth global coordinates system. For example, the transformation may be performed by finding the 3D relation between the IOS camera 160 and the tooth 120. The 3D relationship between the camera and the tooth may be found using, for example, Structure from Motion (SfM) methods or any other suitable methods. Optionally, probe 114 is scanned around tooth 120, for example to gather data with which to construct a 3D model of tooth 120. The 3D model may be stored in coordinates of a tooth global coordinate system.

FIGS. 1A and 1B illustrate exemplary tooth surfaces and shadows in accordance with some embodiments of the current invention. For example, surface 140 (defined by dashed lines) on tooth 120 may be substantially flat in an X-Y plane. For example, the shadow of a linear probe 114 projected on a flat surface 140 may be a substantially straight line 146, as seen in the insert. In FIG. 1B, an exemplary surface 150 on tooth 120 may include a curved surface 152. For example, the shadow 156 of linear probe 114 projected on the curved surface 150 may appear to curve from some viewpoints.

In some embodiments, camera 160 may be placed close to the optical aperture 158, which is defined as the camera lens exit pupil. Alternatively or additionally camera 160 may be located at a larger distance from aperture 158. Optionally relay optics and/or a mirror may be used to convey light from aperture 158 to camera 160. In some embodiments, this may facilitate reducing the size of the intraoral portion of the IOS 102.

In some embodiments, camera 160 may capture images at a high frame rate. For example, a frame rate may range between 500-2000 frames per second (FPS). In some embodiments, an image may be limited to only the shadow and/or additional feature of interest. Limiting images size may facilitate increasing the frame rate of image capture, reducing scan time and/or higher precision. For example, the images may be limited by using only a portion or few portions of the camera image sensor (for example between 0 to 10% and/or between 10 to 30% and/or between 30 to 70% and/or between 70 to 100%). For example, the image may be limited by using Region of Interest (ROI) reading, which is supported by many CMOSs. In some embodiments, ROI reading facilitates higher frame rate. Limited data from an image may take less than 5% and/or between 5 to 10% of the memory space of the original image and/or between 10 to 30% and/or between 30 to 60% and/or between 60 to 90% and/or between 90 to 99% of the memory space of the original image.

In some embodiments, during scanning shadow 144 may be projected on any surface of tooth 120. Optionally, camera 160 images the shadow. For example, shadow 144 may be moved continuously across one or more surfaces of tooth 120. At any surface, the image of the projected shadow is optionally captured by camera 160. The captured images are optionally processed by a processing system 170. Processing system 170 optionally comprises image analysis functionality and/or data processing functionality. Processed data is optionally used for constructing a 3D model of the tooth surfaces.

Figure 3B:
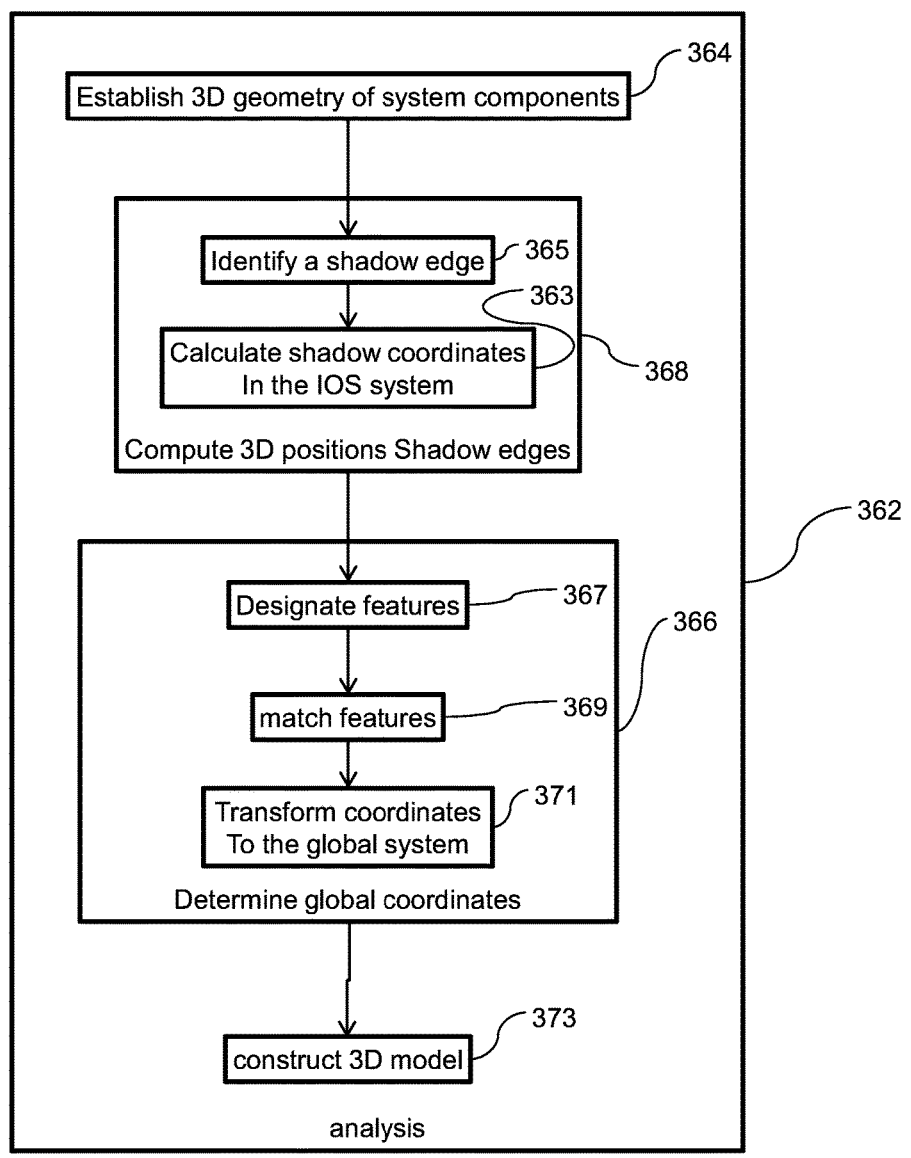
FIG. 3B is a flow chart illustration of further details a method of 3D data from an intraoral scan in accordance with an embodiment of the present invention.

A non-limiting example, the processing algorithm is illustrated in FIG. 3B. In some embodiments, the exemplary process may be performed to obtain a model of a portion of a tooth, a full tooth, few teeth, and/or a full arch.

In some embodiments processing system 170 may include a controller. Optionally, the controller may control parameters related to the light source 116. For example, controller 170 may control the angle of the illuminated light relative to oral-facing surface 110 and/or relative to a surface on tooth 120 and/or controller 170 may control a duration of illumination.

In some embodiments, probe 114 may have some flexibility and/or be deformed from a perfect straight edge. Optionally, markers (for example fiducials) may be marked or attached to the probe. Optionally, by analyzing their location in the image, the location of various portions of the deformed probe 114 may be estimated. Exemplary algorithms for such calculations are described in U.S. Patent publication 2015/0348320.

In some embodiments, contact between a tip of probe 114 and a tooth may be identified based on deformation of probe 114. Method for identifying this contact are described for instance as described in U.S. Patent publication 2015/0348320. In some embodiments, the location 127 where probe 114 tip touches tooth 120 may be included in a 3D model of tooth 120. For example, contact of the tip and the tooth are optionally used to map parts of the tooth that are obscured by blood, fluids or the gums.

In some embodiments, the geometry of the IOS is fixed and/or known. For example, the known geometry may include the 3D relationship between the locations of light source 116, probe 114 and/or aperture 158. In some embodiments, intrinsic parameters of the camera 160, such as equivalent focal length EFL, distortion etc. may be obtained by calibrating the IOS 102 prior to performing a scan. Alternatively or additionally, the calibration information may be obtained during the tooth scan, using suitable methods, for example a bundle adjustment method.

In some embodiments, the probe includes fiducials or markers. Optionally the markers are in the FOV of the camera 160. For example, the distance between a pair of markers may be a known. For example, data about the markers may be used for calibrating a 3D model. Alternatively or additionally, fiducials seen by the camera 160 may be used for identifying probe movements relative to optical aperture 158 for example due to probe distortion. Optionally calculations may be adjusted to compensate for the distortion. Compensation may be added to calculation of the shadow location and/or calculation of the probe tip location.

Probe with Fiducial Markers

Figure 2B:
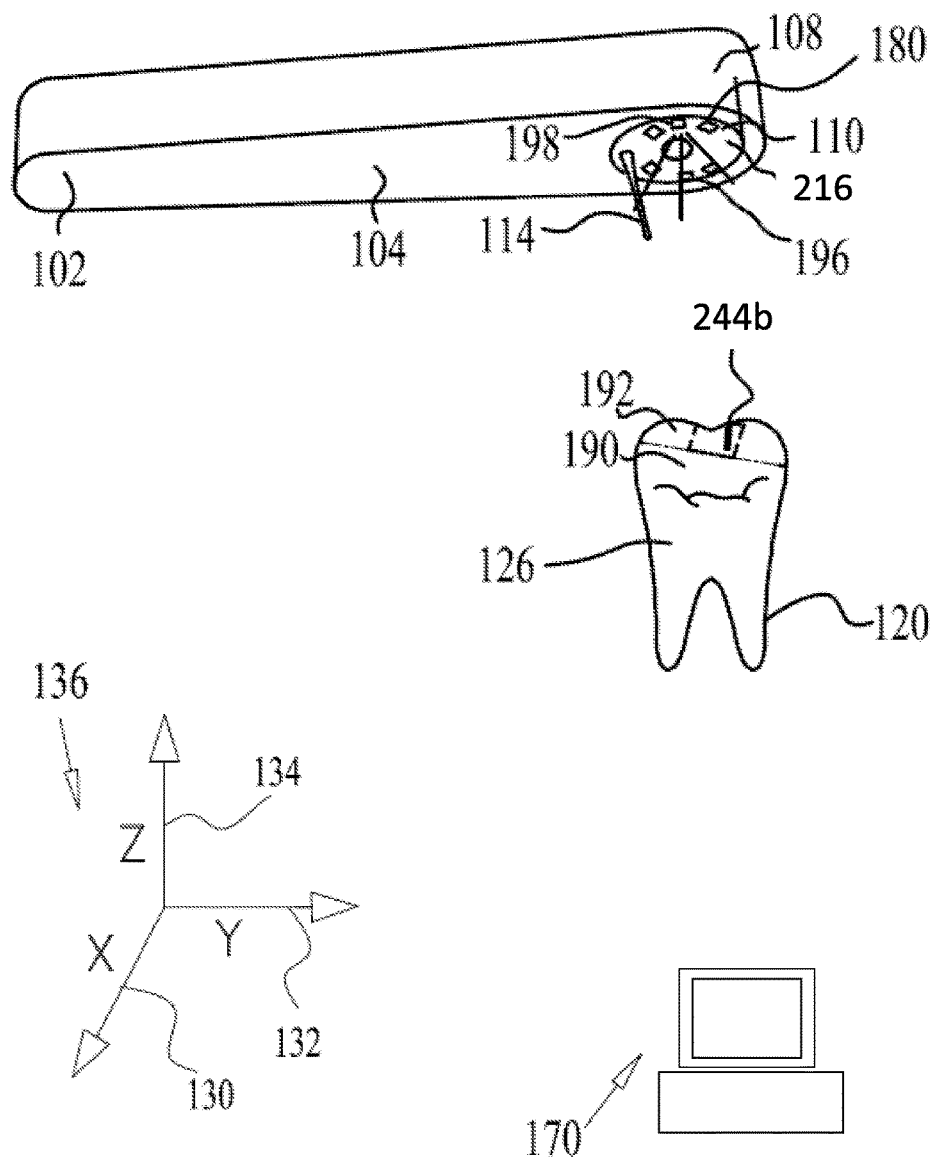

FIGS. 2A and 2B illustrate, an IOS 200 with multiple light emitters in accordance with an embodiment of the current invention. A light source 216 optionally comprises a plurality of light emitters, for example LEDs 180 and/or lasers. Alternatively or additionally, optical fibers with a remote light source's may be used. In the exemplary embodiments of FIGS. 2A and 2B six LEDs 180 are circumferentially arranged on the oral-facing surface 110. It is appreciated that any suitable number of light emitters may be provided and/or may be arranged in any suitable arrangement at any suitable location within the IOS system 200.

In some embodiments, a shadow 244a of probe 114 is cast on a surface of tooth 120 to be imaged. The surface is optionally illuminated by one of LED's 180, selected to cast shadow 244a onto the chosen surface. In some embodiments, controller 170, by aid of the camera 160, may receive a measurement of the spatial orientation (e.g. angle) of the chosen surface relative to the probe 116. The angle may be defined for example by the 3D coordinate system 136. The controller 170 is optionally configured to select the appropriate LED 180, suitably placed relative to the probe 116 to illuminate the surface. Accordingly, the shadow 144 will be cast upon the surface.

In a non-limiting example, a surface of tooth 120 comprises a proximal surface 190 and a distal surface 192. The plurality of LEDs 180 comprises a distally positioned LED 196 and a proximally positioned LED 198. For example as illustrated in FIG. 2A, a chosen surface for imaging may include a proximal surface 190. To illuminate and cast a shadow on proximal surface 190 controller 170 optionally selects to illuminate distal LED 196. A shadow 244a is thus projected on the chosen, proximal surface 190.

FIG. 2B, illustrates an exemplary configuration wherein the chosen surface for imaging is distal surface 192. In some embodiments controller 170 may select to illuminate the proximal LED 198. A shadow 244b is thus projected on the chosen, distal surface 192.

In some embodiments, a user may scan the probe around an object to be scanned. As the user scans the object, the processing unit computes the geometrical relation between the probe 114 and the tooth 120 for each image during the scan and may activate the proper light source 116 accordingly. Thus, the LEDs 180 may be manipulated to illuminate in accordance with the chosen surface of the tooth 120. Optionally, multiple light emitters may be illuminated sequentially. For example, while scanner 200 is scanning around a tooth, different LED's (e.g. LED's 198, 196) of light source 216 may be illuminated. For example, the LED's may be switched in a fast sequence, such that the position of the scanner almost does not change between illumination events. Optionally, the resulting images may be related one to another and/or made into a mosaic to relate (e.g. determine relative position of) features on different surfaces and/or to relate features revealed by different shadow 244a, 244b positions.

FIGS. 2C and 2D illustrate an intra-oral scanner being used to scan tooth 120 while a user probes the tooth 120, for example, under a gum line in accordance with an embodiment of the current invention. Optionally the user scans probe 114 around the tooth close to and/or under the gums, as seen at FIG. 2C. Optionally, a shadow 244c is cast over the wall and/or crown of tooth 120. Processing unit 170 optionally identifies the location of scanned tooth 120 relative to probe 114 and/or the location of the side of tooth 120 relative to probe 114 and/or illuminates tooth 120 from opposite probe 114, to cast a shadow 244c on the scanned surface.

In some embodiments, the user may scan the probe 114 around tooth 120, such that the tip of probe 114 gets below the gums line, for example to scan a subgingival finish line. In some embodiments the probe 114 includes additional features, as seen for example in FIG. 2D. For example, shadow 244c, shown schematically casted over the wall and tooth crown in FIG. 2D, includes additional shadows 244d and 244e cast by fiducial markers 215a and 215b respectively. Optionally markers 215a and 215b are perpendicular to probe 114 direction and parallel to the scan around the tooth direction, the additional depth point obtained from shadow 244d and 244e are out of the plane created by probe 114 and light source and/or may provide 3D information on points on the tooth that are out of aid plane. In some embodiment, different fiducial markers may have different directions. Some of the markers may be positioned to cast shadows when illuminated by one LED 198 while other may be positioned to cast a shadow with another LED 196. Additionally or alternatively, the form of a shadow of the fiducial marker processor 170 may determine the relative direction of the light source with relation to the illuminated surface and/or the direction of the illustrated surface. The 3D information from the shadows of the fiduciary markers may optionally be used, by processing unit 170 to estimate probe and/or IOS movements between the different images.

In some embodiments, more than one LED 180 may be illuminated simultaneously to provide more than one shadow on the surface of the tooth 120.

In some embodiments, more than one LED 180 may be illuminated sequentially synchronized with the camera 160 to provide more than one shadow on the surface of the tooth 120 in separate images. In some embodiments, the sequential illumination may be fast enough to be substantially simultaneous (for the sequential images may be captured in a time small enough that no significant movement occurred in the meantime).

In some embodiments, the light source 116 may be placed on another object away from the IOS 102.

In some embodiments, more than one camera may be used to capture said probe shadow from several angles and improve 3D accuracy. Optionally multiple cameras may take images simultaneously. In some embodiments, more than one camera may be used to capture more and/or better features for estimating the camera pose and tooth 3D surface.

In some embodiments, a pattern projector may be added, such that the image of said pattern projected over at least one tooth may be support the 3D model and camera pose estimation.

In some embodiments, the pattern projector and additional light sources may be used at a certain temporal sequence to combine the depth information achieved by each light source.

High Level Flow Chart

Referring now to the drawings, FIG. 3A illustrates a high level flow chart of a method intra oral scanning using shadows in accordance with an embodiment of the present invention. In some embodiments, a shadow is cast 354 on an intra-oral surface, for example a surface of a tooth. For example, the tooth may be illuminated 352 from an illumination point and/or a shadow may be cast 354 on the surface. For example, the shadow casting object may include a passively occurring object and/or an artificially inserted object. Data from the position of the light and/or shadow is optionally recorded 356. For example, the data may include digital information on the position and/or orientation of a component of the system and/or the shadow. Alternatively or additionally, the data may include an image of an object, a component of the system and/or the shadow. The shape of the surface is optionally determined from the geometry of system and/or the apparent location and/or geometry of the shadow from a defined perspective. For example, the shadow may be imaged using an imager from the viewpoint. The shape of the surface may be determined from the shadow based on knowing the position of the light source, the position and/or shape of the shadow casting object and/or the position of the view point.

In some embodiments, a shadow is cast 354 on a surface to be imaged by illuminating 352 the surface with a light emitter. An object between the illumination source and the surface optionally casts a shadow on the surface.

In some embodiments, an image may be recorded 356 of a location related a shadow on the surface. For example, the location may be at an edge between the shadow and an illuminated region of the surface. In some cases, the edge may be smeared over a region, depending on the size of the illumination source aperture, and the location may be defined at a certain level over the edge gradient. Optionally, the shadow may cover a small portion of the surface, for example between 0 to 5% and/or 5 to 25% and/or 25 to 50% of the surface, ROI and/or tooth may be covered by the shadow. Alternatively or additionally, the shadow may cover a large portion of the surface for example between 50 to 55% and/or 55 to 75% and/or 75 to 90% and/or 90 to 100% of the surface, ROI and/or tooth may be covered by the shadow. Alternatively or additionally, the illuminated region may be within the shadow and/or around the shadow. In some embodiments, the shadow region and illuminated region may both be continuous. In some embodiments, there may be multiple disconnected shadows inside a connected illuminated region. In some embodiments, there may be multiple disconnected illuminated regions inside a connected shadow region. For example, the shadow producing objects may include an area having a hole and the illuminated region may include a spot where light passing through the hole impinges on the surface. For example the shadow casting object include part of housing, wall, probe, and/or special probe with markers.

In some embodiment, a shadow casting object may include a dental probe. Optionally the probe may be imaged 356 (for example using wide enough FOV imager to image the RIO and the probe). Images of the probe may be used as for computing 368 the location of the shadow casting edge. Alternatively or additionally, a shadow of the probe may be imaged 356 while the probe is being used to investigate a sub gingival structure.

In some embodiments, images may be recorded 365 and/or analyzed 362. For example, images of the probe may be used to establish 364 the position of a revealed portion of the probe. Knowledge of the probe geometry may be used to establish 364 the location of a hidden part of the probe (for example the probe tip that may be hidden by blood and/or tissue). For example, the system may establish 364 the location of a probe tip while the tip is in contact with a subgingival point of a tooth. A large number of such images and/or points may be combined to construct 373 a 3D model of a revealed and/or a hidden structure (for example a revealed portion of a tooth and/or a subgingival portion of a tooth).

In some embodiments a probe may have a sensor that senses when the probe contact a tooth (for example a pressure gauge and/or a strain gauge) the imager is optionally in communication with the sensor to image the probe when the tip is in contact with the tooth. Alternatively or additionally, a probe may be connected to an actuator. For example, the actuator may extend the probe tip outward to contact a surface and/or retract the tip to allow the user to move the device for example to investigate another location. The imager is optionally synchronized to the actuator to image the probe and/or the ROI and/or a shadow of the probe when then probe is extended. In some embodiments, said probe length may be controlled to extend or retract according the scanned tooth size.

FIG. 3B is a flow chart illustration of further details a method of 3D data from an intraoral scan in accordance with an embodiment of the present invention. In a non-limiting example, the processing algorithm may include for example, identifying 365 at least one edge of the probe shadow in the image.

In some embodiments, the 3D coordinates of the shadow are calculated 363 relative to a convenient coordinate system. For example, the relative coordinates may be in relation a component of the IOS scanner, for example relative to the light collector (for example an optical aperture thereof). The relative coordinates are optionally computed 363 based on the established 364 geometry of system components (i.e. the 3D relationship between the light source, the shadow casting object, and/or the light collector) in the coordinate system of the light collector. In some embodiments, the relative coordinate system may be relative to a moving object. For example, the coordinates may be relative to the transient position of the scanner. For example, the relative coordinate system of one image may differ from the relative coordinate system of another image.

In some embodiments, reference features are designated 367 and their locations determined 366. For example, features may be designated 367 and/or matched 369 across images. A number of the features may optionally be designated 367 (for example enough objects are designated 367 in order to locate to orient images of the entire ROI) as reference features and/or the global location of other objects may be found from relative position with respect to the reference features.

In some embodiments, features on teeth portion or gums viewable in the image are designated 367. For example, feature extraction may be done by any suitable computer vision algorithms for feature extraction. An example of such an algorithm includes the Scale-Invariant Feature Transform (or SIFT).

In some embodiment, features designated 367 in different images are matched 369. Matching 369 optionally correlates all the features together, for example, using methods know in the art, such as Random sample consensus (RANSAC) to remove outliers and find a camera 3D translation and rotation that fits the feature matching. Once the rotation and translation of the camera is established 364 for each frame, all the frames may optionally be aligned to a single coordinate system. For each image, the relative coordinates and/or the camera location may be transformed 371 into the unified 3D coordinates. Motion of the camera relative to the teeth is optionally defined and/or images may be corrected for this motion. Defining and/or correcting for camera motion may be performed for example by suitable method for computer vision such as the Structure from motion (SfM), bundle adjustment, least squares, RANSAC, etc. Exemplary algorithms optionally use feature matching to solve for the camera translation and rotation (camera pose) for each frame.

In some embodiments, images may be combined and/or stitched together. For example 3D information on the tooth surface obtained from each image of the probe shadow based on the translation and rotation of the camera may be put together to build 373 a 3D model of the oral cavity or parts thereof. The features, which were matched between the images, are optionally added to the 3D model as well.

In some embodiments, the exemplary process may be performed to obtain a full tooth, or few teeth, or a 3D model of the full arch.

Method of Scanning with a Scanner Having Fixed Probe, LED and Imager

FIG. 4 is a flow chart illustration of a method of modeling a tooth while investigating 451 a tooth with a scanner including a dental probe in accordance with an embodiment of the present invention. The scanner optionally includes a light source (for example an LED) and an imager. Optionally, while a user investigates 451 the surface, the light source illuminates 352 the surface and casts 354 a shadow of the probe onto the surface. The imager optionally captures 456 an image of the surface, the shadow and/or a portion of the probe. Image analysis optionally determines the geometry of the surface.

In some embodiments, the scanner may have the form of a dental probe and associated handle. A user (for example a dentist and/or a dental assistant) optionally investigates 451 a region of a tooth using the probe. For example, by placing tip of the probe in contact with the tooth, the user also positions the scanner in front of a surface of the tooth with the LED and the imager pointed toward the surface. For example, the LED may be located on the scanner in a region between the user and the probe such that the LED illuminates 352 the tooth surface. For example, the LED is directed also to illuminate the probe and thereby cast 354 a shadow of the probe on the surface. Optionally with the LED located in a region between the user and the probe, the shadow of the probe is pointed away from the user reducing inconvenience that the shadow may cause the user. Illuminating 352 the probe and tooth optionally serves the user for example illuminating the tooth on which he is working and/or illuminating markers (for example measurement marks) on the probe.

In some embodiments, while the user is investigating 451 a tooth, the imager captures 456 images of the illuminated surface of the tooth and/or the probe and/or the shadow. Images are optionally stored and/or sent to a processor for analysis 362. Optionally the FOV of the imager is large enough that each image contains features that will be used as reference features. In some embodiments, designated features of a previous oral scan may be used to navigate and/or locate objects in the oral cavity. Alternatively or additionally, the image data will be used to identify reference features that occur in multiple images and/or are used to orient images and/or establish the relative positions of images and/or system components during the scanning.

In some embodiments, as the user continues 358 to investigate 451 the tooth, he reposition 460 the scanner, repeating the imaging process, until he covers an entire region of interest ROI. As the user traverses the ROI so the scanner captures 456 images of the ROI from various perspectives.

In some embodiments, analysis 362 includes establishing 364 the 3D positions of system components, for example the sensor, the light source and/or the probe. For example, in each image, intra oral features may be designated 366 as reference features. The locations of the intra oral features may be used to establish 366 the position of the imager with respect to the oral cavity and/or to determine 368 the location of measured features in the entire oral cavity and/or when combining images to build 373 a 3D model of multiple surfaces (for example an entire tooth and/or an arch and/or a set of teeth).

In some embodiments, images from the scanner are analyzed 362. For example, analysis 362 may be performed during post processing. Alternatively or additionally, images may be analyzed 362 in real time. For example, by the time the user has finished his investigation 451, the processor may have analyzed 362 the images and may present the 3D model to the user. Alternatively or additionally, analysis may identify regions of the tooth that are not properly mapped (for example regions where the data is not dense enough and/or where different images resulted in different measurements leaving a large margin of error in the measurements. The processor may warn the user that he should continue 358 scanning to repeat scanning the improperly mapped region. Optionally a warning may be issued earlier in the scanning process, for example after establishing camera movement 364, designating a reference object 366 and/or even prior to image analysis 362.

In some embodiments, the 3D positions of system components may be established 364 during analysis. Stored images are optionally analyzed 362 to designate 366 reference features. For example, reference features may include identifiable features that are fixed in the oral cavity and/or apparent in more than one image. For example, from the positions of the reference features multiple images may be co-oriented. Based on the orientation of each an image to the reference features, the position of the imager is optionally established 364.

In some embodiments, the position and/or orientation of the light source and/or the probe may be established 364 based on the position and/or orientation of the imager and a known relative position of the components. For example, the position of the LED, imager and/or a base of the probe may be fixed into the scanner such that their relative positions are known. The original and/or unstressed shape of the probe may also be known such that the unstressed position of the entire shadow casting object is known. For example, in some embodiments the probe tip may move by between 0 to 0.05 and/or from 0.05 to 0.1 mm and/or between 0.1 to 0.5 mm to the side when force is applied on the tooth. Optionally, images of the probe and/or its markers may be used to determine a deviation from its unstressed shape.

In some embodiments, based on the positions of the LED, the imager and/or the position and/or shape of the probe, and/or the orientation of the image with respect to a reference feature, the location of a point on the shadow on the surface is computed 368 with respect to the reference feature. Optionally, the positions of a large number of points on the surface are calculated 368 and correlated to build 373 a 3D model of the tooth.

In some embodiments, shadows cast 354 by additional object may be used to determine the shape of the tooth. For example, a concave portion of a tooth surface may cast 354 a shadow on itself. The shape of the shadow under different angles of illumination may help determine the geometry of the surface.

In some embodiments, an intra-oral scanner may be used to locate hidden intra-oral features. For example, when a user is probing a hidden object (for example a subgingival portion of a tooth and/or the interior of a hole in the tooth), the known position of the probe (identified for example from an image) and/or geometry of the probe (optionally based on the unstressed geometry and/or corrected for deviations from the unstressed geometry) may be used to determine the position of a hidden point that is in contact with the probe tip.

Method of Scanning with a Scanner Having a Fixed Probe, Multiple Light Emitters and an Imager FIG. 5 is a flow chart illustration of a method of modeling a tooth while a investigating a tooth 451 with a scanner including a dental probe and multiple light emitters in accordance with an embodiment of the present invention. The scanner optionally includes multiple light sources (for example one or more optical fiber light guides connected on one end to a light source emitting light from the other end and/or one or more LED's) and an imager. Optionally, while a user investigates 451 a tooth, one of the light sources illuminates 352 the surface of the tooth and/or illuminates the probe casting 354 a shadow of the probe onto the surface. The imager optionally captures 456 an image of the surface, the shadow and/or a portion of the probe. Image analysis 362 optionally determines the geometry of the surface.

In some embodiments, as the scanner is positioned and repositioned 460 in the oral cavity, the orientation of the scanner with respect to the ROI may changes. Optionally, for each orientation of the scanner at least one of the light emitters is properly oriented to illuminate 352 the surface and/or the probe to cast a shadow on the surface. For example, as the scanner passes to the left side of a tooth ROI, a light emitter on the right side of probe is activated such that the ROI is illuminated and a shadow of the probe falls on the ROI. Optionally selecting of the proper light source is done automatically. For example, a processor may use cue's from the orientation and/or movement of the scanner to determine what the user is investigating 451. Optionally or additionally, the processor may recognize landmarks in the images produced by the imager in order to navigate in the oral cavity and track the orientation between the scanner and the ROI. Optionally or additionally, the processor may identify the scanned tooth. The processor may select a light emitter to illuminate the tooth and provide a shadow on the tooth. Alternatively or additionally, the processor may use cues from the images to determine which image contains the shadow and/or which light emitter is producing a shadow that is detected on the surface of the ROI. Alternately or additionally, the user may manually select 561 light sources to illuminate an area where he is working and/or the light source may be arranged so that the shadow of the probe falls on the illuminated region.

In some embodiments, separate light sources may be selected 561 successively. For example, different light sources may be activated and/or deactivated and images made be taken of the system with lighting from various angles. In some of the images, the shadow of the probe may fall in the ROI. These images are optionally selected for full processing, for example to determine the shape of the surface of the ROI. In other images, the shadow may not fall in the ROI. These images are optionally discarded. Alternatively, images where the shadow does not fall with the ROI may be processed for example for navigation and/or recognition of reference features.

In some embodiments, for more than one light emitter, the shadow of the probe may be cast 354 onto the ROI. Optionally, by switching light sources, the shadow is repositioned 460 within the ROI. Optionally by switching quickly (for example over a time period of less than 1 msec and/or between 0.001 to 0.1 sec and/or between 0.1 to 10 sec) the shadow will be repositioned 460 with position of the scanner and oral cavity substantially unchanged. For the sake of this disclosure, images taken within a time period where changes in the system and/or orientation are less than an error tolerance of the system may be described as having been made substantially simultaneously. For example, for two images taken substantially simultaneously may be used to determine a spatial interrelationship between different points and/or feature measured on different shadows.

In some embodiments, flashing on and off of different light sources from different angles may disrupt and/or disturb a user. Optionally to avoid such disruption, the light source may be in an invisible frequency (for example infrared and/or ultraviolet). For example, the user may illuminate the ROI as he likes with visible light while the scanner illuminates 352 and/or captures 456 images of light on a different wavelength. Alternatively or additionally, the light emitters and/or imager may be tuned to a narrow frequency band. The user whom may work with a constant wide frequency light source may not be bothered by flashes of highly concentrated narrow frequency radiation while the highly focused imagers may be immune to the wide band noise produced by the user's illumination. Alternatively or additionally, flashes of illumination and/or images synchronized and/or may be made quickly to reduce disruption to the user. For example, the flashes length may be less than a subject awareness limit and/or an objective awareness limit. For example, flashes may last for less than 1 ms and/or between 1 to 20 ms and/or between 20 to 50 ms and/or between 50 to 100 ms and/or greater than 100 ms.

Method of Scanning Semi-Passively

FIG. 6 is a flow chart illustration of a semi-passive method of modeling a tooth while a investigating a tooth in accordance with an embodiment of the present invention. The scanner optionally includes a one or more imagers. Optionally, while a user investigates the ROI he casts 354 a shadow on a surface of the ROI (for example the shadow may be cast 354 by a dental probe). An imager optionally captures 356 an image of the ROI, the shadow and/or a portion of the probe. Image analysis 362 optionally determines the position of the probe and/or the geometry of the surface.

In some embodiments, an imager may be mounted on a dental tool. For example, an imager may be mounted on a handle of a conventional light emitter such as a dental mirror. The user working in a usual conventional fashion positions 651 the mirror in front of a ROI and/or illuminates 352 the ROI.

In some embodiments, the user works with a tool of his choice, for example a conventional dental probe. The user in the course of his work investigating the ROI introduces 653 the probe between the light emitter and the ROI casting 354 a shadow on a surface of the ROI. In some embodiments, as the user moves the mirror and/or the probe, the shadow moves 660. Optionally as the user scans the teeth with the probe, the shadow is also scanned across the teeth.

In some embodiments, the imager is configured to capture an image 356 of the surface of the ROI, the shadow and/or the probe. For example, the imager may be directed toward a region illuminated 352 by light reflected from the mirror. For example, when the user positions 651 the mirror in front of the ROI he is also positioning 655 the light collector in front of the ROI. Alternatively or additionally, the imager may have a wide FOV such that it captures images 356 of the surface, the shadow of the probe, another shadow, the probe and/or a reference feature from a range of orientations.

In some embodiments, as the user works, continuing 358 to investigate the ROI from various perspectives, he moves the mirror and/or the probe thereby moving 360 the shadow over the surface of the ROI. While the user is working, the imager is capturing images of the ROI and the shadow from the various perspectives and/or over various locations of the surface of the ROI.

In some embodiments, an additional imager may be included. For example, an imager may be supplied outside an oral cavity and/or not facing the ROI. For example, an additional imager may be mounted on a dental lamp (optionally the viewpoint of the additional imager may substantially coincide with the lamp. Alternatively or additionally, the location of the imager may be offset from the lamp. For example, mounting the additional imager with a view point coinciding with the lamp may help keep the additional imager directed at the intended objects (for example the ROI, the mirror, and the probe). Alternatively or additionally mounting the additional imager offset from the lamp may facilitate imaging the shadow. The imager on the lamp may optionally catch an image of the light emitter (for example he mirror), a light collector (for example the imager mounted on the mirror handle) and/or the shadow and/or the ROI (for example as it is reflected in the mirror and/or directly in the case where the user is investigating an area exposed directly to the light.

In some embodiments, an additional imager may be used to for binocular location of objects and/or of locations on a surface. For example, two imagers may be located outside of the oral cavity. Optionally the relative orientation of the two imagers may be known and/or fixed. From the two images captured 356 at different viewpoints, the exact location of an object in the images may be computed. For example, the location may be computed for a dental mirror and/or intra-oral sensor and/or of a reference feature in the oral cavity. For example, the dual external cameras may give the location of the oral cavity and at least some of the time of the mirror and/or intra-oral imager. Optionally the dental mirror and/or the external lamp and/or one, some or all of the imagers may include an accelerometer and/or gyroscope for tracking the absolute location and/or motion of the component. For example, when the image data is not sufficient to track the locations of components, the absolute location and/or movement data may be used to fill in and/or preserve measurement accuracy.

Method of Scanning when Navigation Data is Available

FIG. 7 is a flow chart illustration of a method of modeling a tooth when navigation data is available on the oral cavity in accordance with an embodiment of the present invention. Optionally, in some cases an object may be investigated in an oral cavity for which navigation data is available. For example, when placing a new crown in an oral cavity where work was done previous, such that detailed knowledge of much of the oral cavity is available, but it is desired to map changes for example to model a portion of the tooth that has been prepared from the crown. Alternatively or additionally, an intra-oral scan may be performed in an oral cavity that has been marked previous, for example with powder that may provide features on the tooth and/or by adding a mark and/or a fiducial marker.

In some embodiments, navigation information may be obtained using tracking methods known in the art, for instance active electromagnetic tracking that use at least one source coil that transmit electromagnetic radiation and at 3 orthogonal receiving coils that senses the direction and distance to said at least one source. One of them may act as a stable reference and the second may be attached to the IOS.

In some embodiments, navigation information may be obtained using additional sensors, such as gyro, accelerometer, digital compass etc.

In some embodiments, navigation information is used to establish 764 a location of a scanner and/or a shadow casting object and/or an imager and/or to determine 368 the location of a shadow during scanning. Alternatively or additionally, markers may be used to simplify analysis 362 of data (for example markers may be used to orient different images one to another without requiring separate identification of reference features). In some embodiments the entire analysis may be performed in real time for example while a user is investigating sub gingival structures the scanning system may model super gingival structure and/or relate super gingival structures to sub gingival structures detected by a probe.

Method of Scanning Employing Binocular Stereo Vision

FIG. 8 is a flow chart illustration of a method of modeling a tooth using multiple overlapping image sensors in accordance with an embodiment of the present invention. For example, two or more overlapping image may be capture 856 of a ROI from different viewpoints. Optionally a shadow on the surface may facilitate identification of common points in the images. The location of the points may optionally be determined by stereo vision methods (e.g. stereo triangulation), based on a knowledge of the location of the viewpoints. Multiple images are optionally used to locate points on a surface when the exact location of a light emitter and/or a shadow casting object is not precisely known. Alternatively or additionally multiple images may be used to verify, adjust, and/or calibrate a system of locating points based on a single viewpoint and known location of the shadow casting object and the light source. Alternatively or additionally binocular stereo vision methods may be used to fill in data in areas where there is a high margin of error in other measurement methods. Optionally, additional matching features, which are designated in the overlapping images, may be added to the 3D model.

In some embodiments, the location of a point may be determined 868 from two overlapping images acquired from two different viewpoints. Optionally the locations of the viewpoints may be established 864.

In some embodiments, a cast shadow may mark a location. For example, a surface of a ROI may lack easily located features (for example, a surface of a tooth prepared for a crown may be smooth and/or monochromatic). Optionally the surface of the ROI may be imaged 856 by two overlapping images from the two viewpoints. Optionally a feature of a shadow may supply a feature that may be recognized in two pictures. Comparison of the two images may determine 868 the 3D location of the feature for example employing binocular stereo vision methods.

In some embodiment, two imagers may be mounted on a single scanner and/or dental tool for binocular imaging. Optionally the imagers have a fixed relative position on the tool. In some embodiment, more than two imagers may be mounted the scanner and/or dental tool. Extra imagers optionally add additional viewpoints and/or improve accuracy and/or imaging FOV. Alternatively or additionally, an imager may be mounted on a stable mounting (for example a dental lamp and/or a mechanical arm) and/or on a dental tool. For example, the spatial location of a tool may be known by inertial navigation (for example a tool may include an accelerometer and/or a gyro). For example, the spatial location of a tool may be known by designating reference features in an image made by the sensor. For example, the spatial location of a tool may be known with respect to designated reference features in an image of the tool.

Scanner with Multiple Shadow Casting Objects

FIG. 9 is a schematic illustration of a scanner having multiple shadow casting objects in accordance with an embodiment of the present invention. For example, a probe 114 and two shorter shadow casting rods 914a and 914b cast shadows 244c, 944a and 944b respectively on tooth 120. The presence of multiple shadows may facilitate faster and/or more accurate scanning of a tooth. Optionally, probe 114 is long enough to investigate a sub gingival zone of tooth 120. For example, while a user is investigating a sub gingival zone with probe 114, the system is measuring revealed areas of the tooth using shadows 244*c*, 944*a* and 944*b*. Optionally the system may also track the location of the tip of probe 114.

Simple Scanner System

Figure 10:
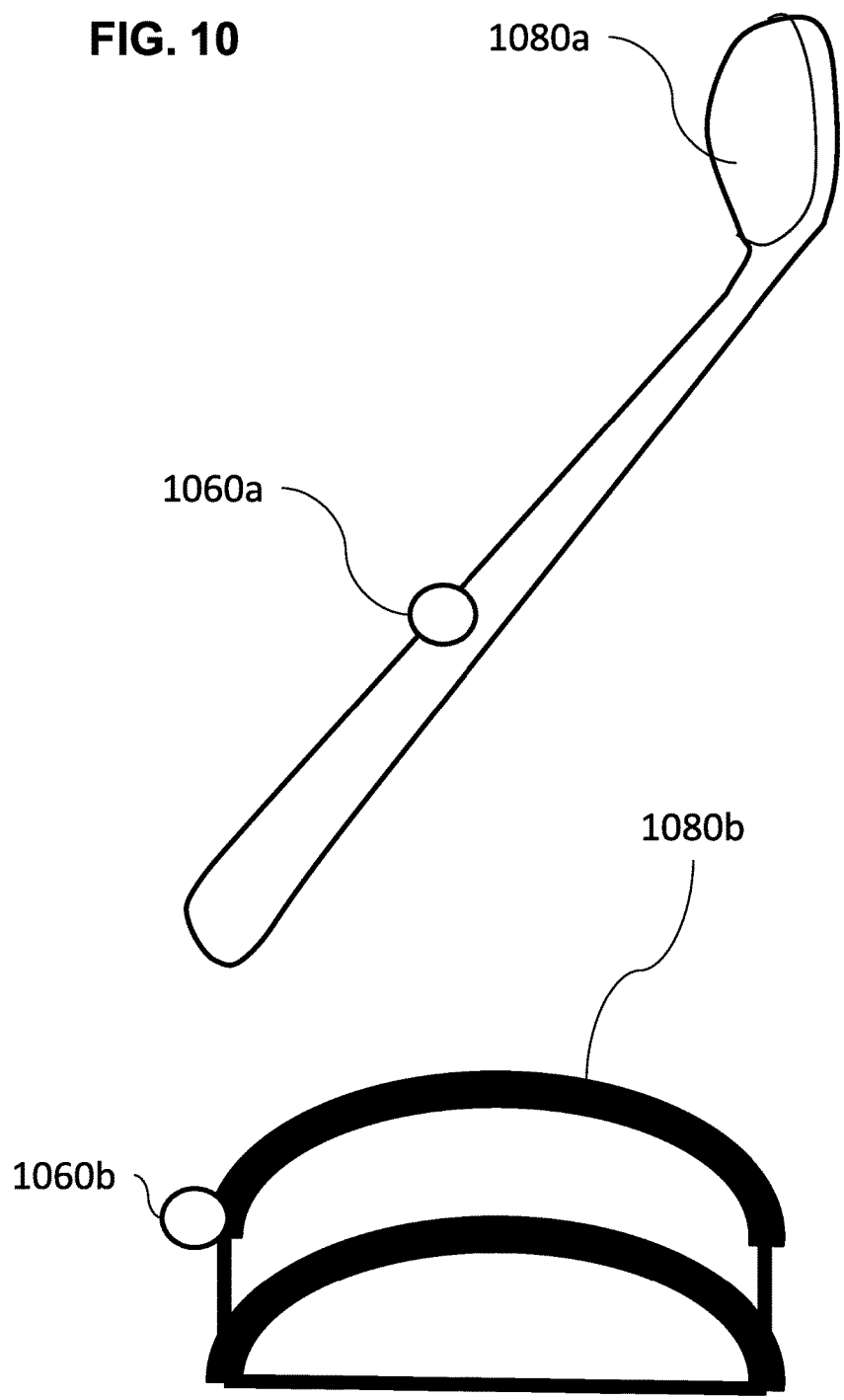
FIG. 10 is a schematic illustration of a scanning system having multiple imagers in accordance with an embodiment of the present invention.

FIG. 10 is a schematic illustration of a scanning system having multiple imagers in accordance with an embodiment of the present invention. For example, a first imager 1060*a* may be placed on a handle of a dental instrument (for example a light emitter, mirror 1080*a*). A second imager 1060*b* is optionally located on a light source, for example dental lamp 1080*b*. Imager 1060*a* may capture images of a surface of a ROI and a shadow. Another option is that light emitter is on the mirror such that mirror body cast shadow on the tooth on the one hand and may be used also for better illumination for the user's vision. For example, the shadow may be cast by a conventional dental instrument as a dentist works in an oral cavity. Imager 1060*b* may collect images of reference features and/or mirror 1080*a*. For example, images from imager 1060*b* may establish the location of mirror 1080*a* and or imager 1060*a*. In some cases imager 1060*b* may capture images of a surface of a ROI and/or a shadow cast thereon. In some embodiments, overlap of images from imagers 1060*a* and 1060*b* may be used for binocular stereo vision methods. In some embodiments images from imagers 1060*a* and 1060*b* may be processed, for example by processor 170. In some embodiments, other examples of dental tools may cast shadows and/or may be shadow casting objects, for example a dental drill or turbine.

Scanner with Multiple Imagers

Figure 11:
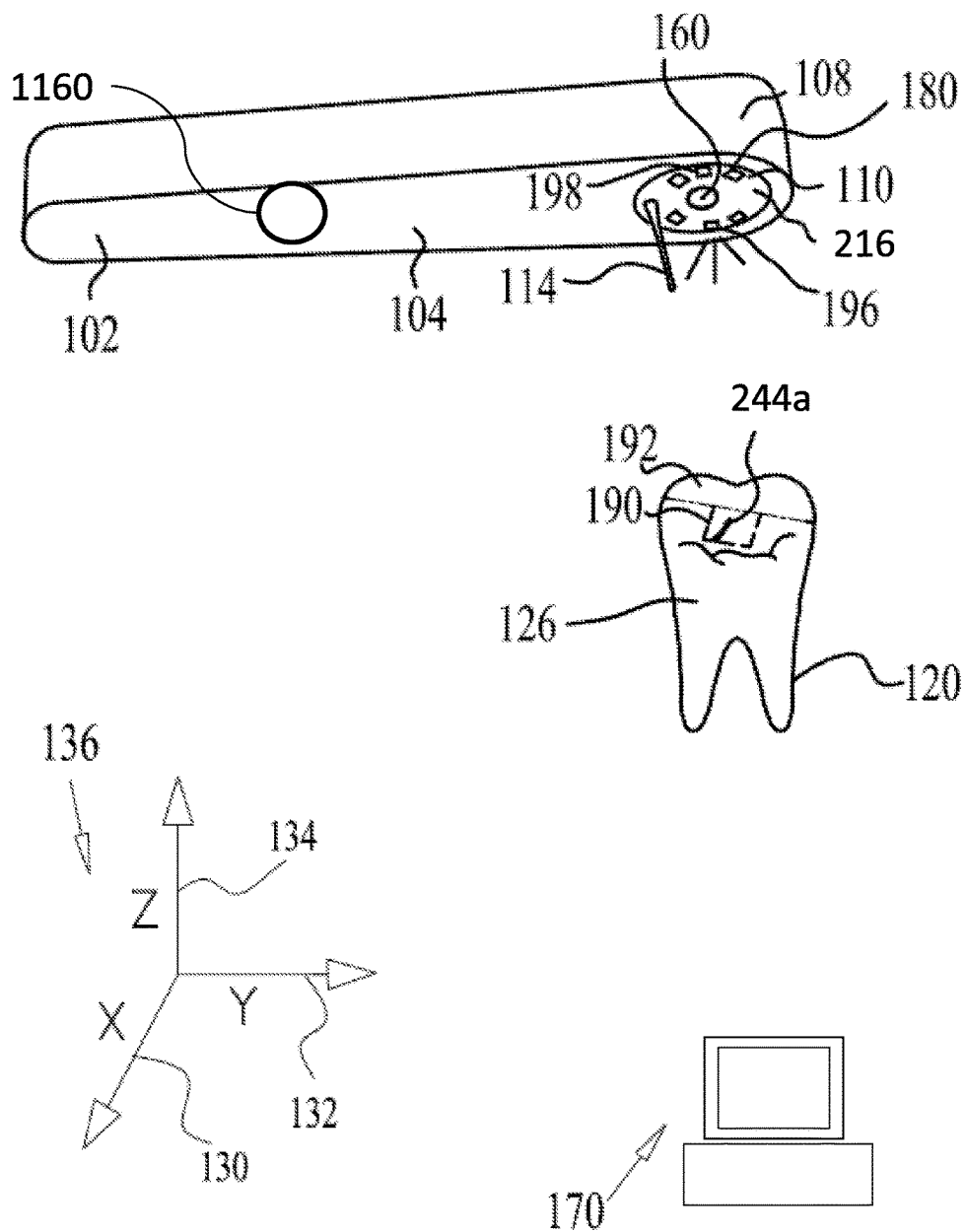
FIG. 11 is a schematic illustration of a scanner having multiple imagers in accordance with an embodiment of the present invention.

FIG. 11 is a schematic illustration of a scanner having multiple imagers in accordance with an embodiment of the present invention. For example, images may be taken simultaneously of a ROI and/or a shadow by a narrow FOV imager 160 and a wide FOV imager 1160. Overlapping areas of the images are optimally used for stereo vision to locate objects and/or surfaces. Additionally or alternatively, images from wide FOV imager 1160 may be used for designate and/or orient to reference features.

Scanner

Figure 12:
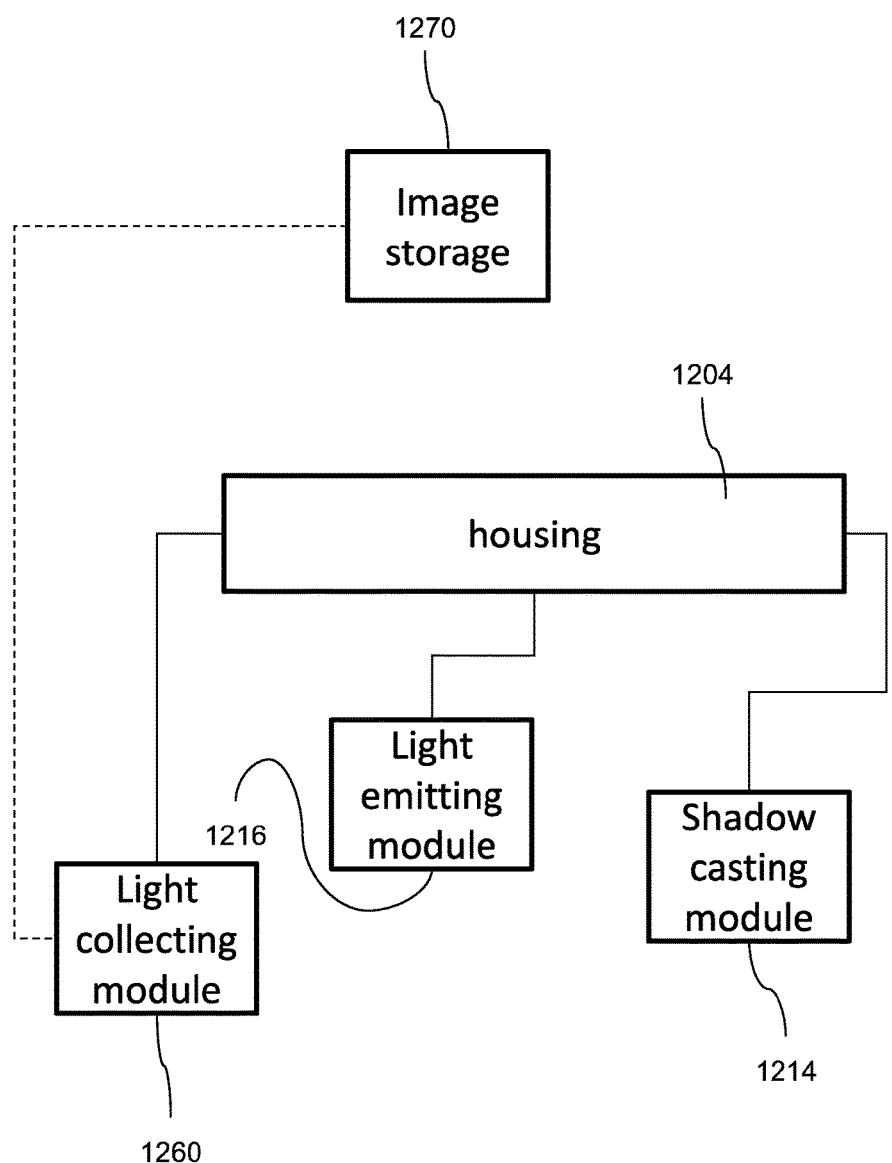
FIG. 12 is a block diagram of an intraoral scanner in accordance with an embodiment of the present invention.

FIG. 12 is a block diagram of a scanner in accordance with an embodiment of the present invention. In some embodiments a scanner may include a housing 1204. A portion of the housing is optionally configured to fit in an oral cavity of a subject. A second portion of the housing is optionally configured for manipulation by a user. Optionally a shadow casting module 1214 is connected to the housing. For example, shadow casting module 1214 may include a dental tool. Optionally the shadow casting module or at least a portion thereof is connected to the portion of the housing fitting in the oral cavity. Optionally the shadow casting module or at least a portion thereof fits in the oral cavity. Optionally a light emitting module 1216 is connected to the housing. Optionally the light emitting module 1216 is configured to project light over a portion of shadow casting module 1214 onto a ROI (for example the surface of a tooth or gums). Optionally a light collecting module 1260 is connected to the housing and/or directed to capture an image on the ROI and/or the shadow and/or a portion of the shadow casting module 1214. Optionally, the captured image is sent over a communication pathway to an image storage module 1270. Image storage module 1270 optionally include a processor to analyze images and/or control other components of the system, for example light emitting module 1216 and/or light collecting module 1260 and/or shadow casting module 1214.

In some embodiments, the shadow casting module 1214 will cast a single connected shadow. In some embodiments, the shadow casting module 1214 will cast multiple disconnected shadows and/or a complex shadow (for example including a projection of a fiducial marking). In some embodiments, the light emitting module 1216 includes a single light emitter. In some embodiments, the light emitting module 1216 includes a multiple light emitters. For example, each of the multiple emitters may illuminate different regions and/or cast a shadow on a different region.

In some embodiments, the light collecting module 1260 includes one or multiple light imagers and/or multiple optical apertures. For example, each of the apertures may image a different region and/or multiple apertures may image the same region from different angles for example allowing binocular and/or 3D imaging. Optionally some light emitters may have larger FOV's than others.

Light Collecting and Emitting System

Figure 13:
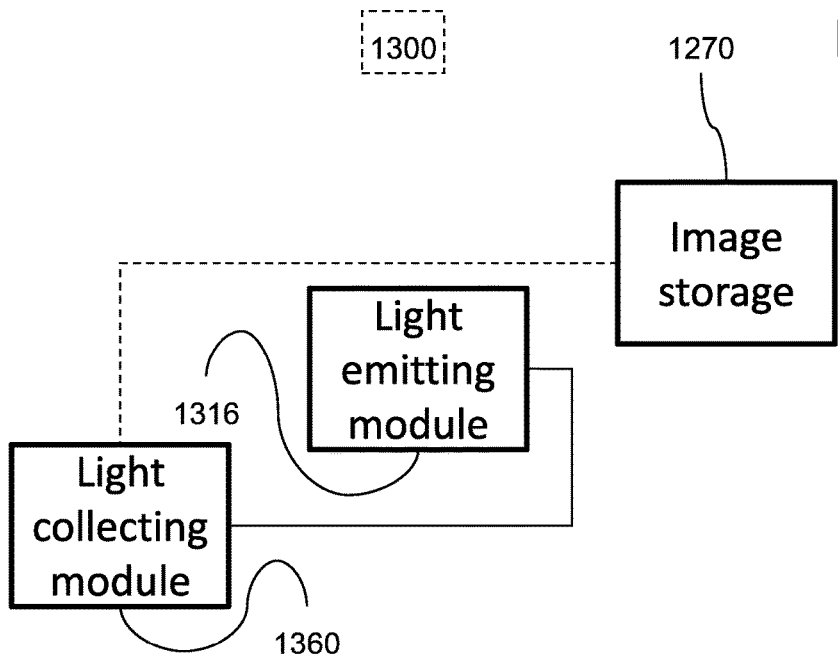
FIG. 13 is a block diagram of a portion of an intraoral scanner system in accordance with an embodiment of the present invention and FIG. 14 is a block diagram of a portion of an intraoral scanner system in accordance with an embodiment of the present invention.
Figure 14:
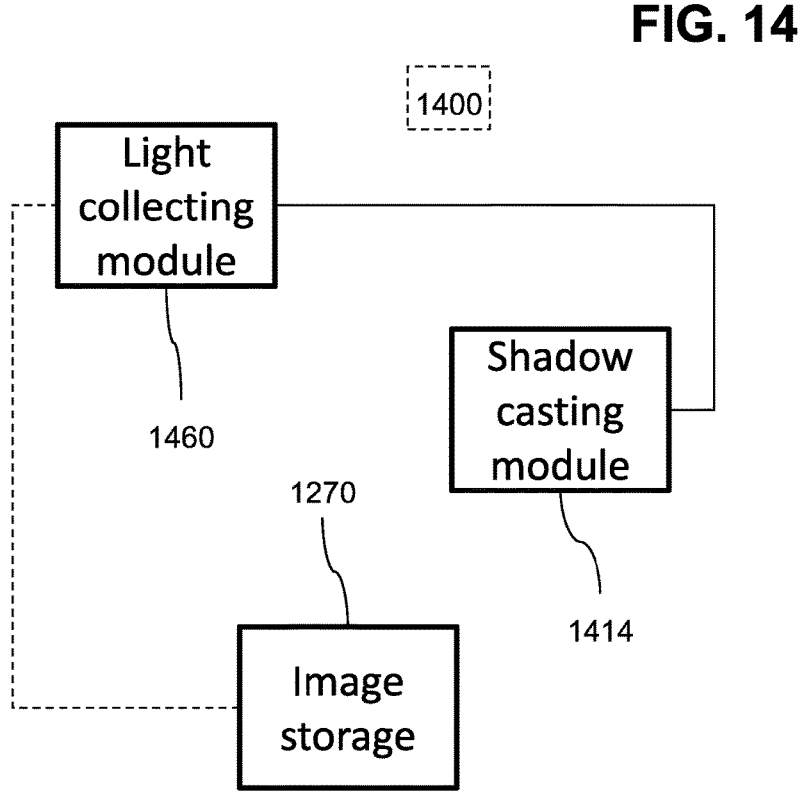

FIG. 13 is a block diagram of an independent system 1300 including a light collection module 1360 and emitting module 1316. For example, the light collecting and emitting system 1300 may be used with a separate shadow casting object, for example a natural part of the oral cavity and/or a conventional dental tool and/or a custom dental tool (for example system 1400 as illustrated in FIG. 14). For example, light emitting module 1316 optionally illuminates a ROI and/or a shadow casting object thereby created an illuminated ROI and shadow on the ROI. Light collecting module 1360 optionally images the ROI and the shadow. Image storage module 1270 stores images and/or analyzes images. For example when used with another imaging tool system 1300 may be used for navigation (e.g. tracking a light emitter, a light collector and/or a shadow casting object). For example, when combined with another light collector, system 1300 may produce binocular images from which 3D locations may be calculated.

Light Collecting and Shadow Casting System

FIG. 14 is a block diagram of an independent system 1400 including a light collection 1460 and shadow casting 1314 module. For example, system 1400 may be used with a separate light emitter. For example, shadow casting module 1414 optionally includes a dental tool for working on a ROI. Light collecting module 1460 optionally images the ROI and a shadow of object 1414. Image storage module 1270 stores images and/or analyzes images.

It is expected that during the life of a patent maturing from this application many relevant dental instruments, imagers, light emitters will be developed and the scope of the terms are intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of imaging a tooth comprising:
   providing an intraoral scanner including a head portion having a shadow casting object, a light emitter, and an imager having known relative positions; wherein said head portion is sized and shaped to fit into a mouth of a subject;
   moving said head portion around a perimeter of a tooth to scan a plurality of portions of an exterior surface of the tooth, wherein for each portion of said plurality of portions of said tooth, scanning comprises:
   illuminating said portion of the tooth with said light emitter;
   casting a shadow on said portion of the tooth by positioning said shadow casting object between said light emitter and said tooth;
   imaging said portion of the tooth, including at least a part of said shadow, to produce one or more respective images of light collected from said portion of the tooth including at least two points on said portion of the tooth;
   determining a pose of said imager from each of said one or more images;
   deriving a position of a said light emitter and said shadow casting object from said pose of said imager and said known relative positions;
   identifying a 3D orientation of a ray of illumination from the light emitter intersecting said shadow casting object and defining an edge of the shadow based on said pose of said imager and said known relative positions; and
   ascertaining a 3D location of each of said two points from said 3D location of said intersection, a location of said shadow in said image and a location of each of said two points in said image.

2. A method according to claim 1, wherein said determining comprises determining a movement of said imager from said image and at least one previously acquired image of a previous portion of said plurality of portions of said tooth.

3. The method of claim 1, further comprising:
   storing a plurality of further images of an oral cavity containing the tooth;
   designating at least one reference feature in said plurality of further images and
   calculating said location of said at least two points related to said shadow with respect to said at least one reference feature.

4. A method according to claim 3, wherein said reference feature is at least a portion of at least one of a tooth or gums.

5. A method according claim 1, wherein said shadow casting object includes a dental probe.

6. A method according to claim 1, wherein said shadow casting object includes a dental drill.

7. A method according to claim 1, wherein said shadow casting object includes a component of a dental tool used for a dental procedure.

8. A method according to claim 1, wherein said determining comprises determining a relative position of an imager used for imaging and said tooth and said shadow casting object.

9. A method according to claim 8, further comprising identifying a deformation of said shadow casting object.

10. A method according to claim 1, wherein said imaging is performed with an imager and further comprising identifying a shape of a portion of said shadow in said image and identifying a point of intersection between a line of sight of the imager and a line of illumination of the light emitter defined by the shadow and said tooth based on said shape.

11. A method according to claim 1, wherein said determining comprises determining the location of a line comprising a plurality of points in a same cast shadow.

12. A method according to claim 1, wherein imaging comprises imaging a plurality of teeth simultaneously with said part of said shadow.

13. A method according to claim 1, wherein illuminating comprises selecting an illumination point to cast said shadow on of said shadow casting object on a preselected portion of said tooth.

14. A method according to claim 13, wherein selecting comprises selecting a plurality of illumination points, applied in sequence to cast said shadow of said shadow casting object located at a predetermined location onto more than one of said plurality of portions of said tooth.

15. The method of claim 13, wherein said head portion includes multiple light emitters and wherein said selecting an illumination point is from said multiple of light emitters.

16. A method according to claim 15, wherein selecting an illumination point to cast said shadow on said preselected portion of said tooth, includes identifying 3D location of said shadow casting object and said plurality of light sources and said preselected portion of the tooth; and wherein said selecting an illumination point is for improving shadow image obtained by said imager.

17. The method of claim 16, wherein said improving includes at least one factor selected from the grouping consisting of increasing a contrast between a shaded and an illuminated area, decreasing a measurement error, and increasing a baseline.

18. A method according to claim 1, wherein said imaging includes imaging from a viewpoint and wherein determining includes:

sighting said point from a viewpoint to determine a line of sight from said viewpoint to said point; and establishing a relative location of said shadow casting object with respect to said viewpoint and wherein said determining is based on said relative location and said line of sight.

19. A method according to claim 1, wherein said determining includes:

sighting said point from each of two viewpoints to determine a line of sight from each said viewpoint to said point; and establishing a relative location of two viewpoints and wherein said determining is based on said relative location and said line of sight from each said viewpoint.

20. The method of claim 1, further comprising:

establishing a relative position of the shadow casting object with respect to said light emitter.

21. The method of claim 1, wherein said location is with respect to said imager.

22. The method of claim 1, wherein said shadow casting object, an imager used for imaging and a light emitter used for illuminating are fixedly coupled and inserted as a unit into an oral cavity containing said tooth, with said shadow casting object extending away from a housing of said unit.

23. The method of claim 1, wherein said location is with respect to a shadow casting object.

24. The method of claim 1, comprising storing at most a limited representation of said image after said determining.

25. The method of claim 1, wherein said imaging is performed by an imager that is distanced between 1-10 mm said light emitter.

26. The method of claim 1, wherein said imaging is performed by an imager that is distanced at least 0.5 mm from at least one plane defined by said light emitter and two points on an edge of said shadow casting object.

27. The method of claim 1, further comprising:

designating a plurality of reference features in an oral cavity that includes said tooth and wherein said determining a camera pose includes calculating said pose with respect to said reference features based on a location of at least three of said reference features in said image imaged from said pose.

28. The method of claim 27, wherein as least one of said plurality of reference points is not on said tooth.

29. The method of claim 1, wherein a portion of the shadow casting is distanced from the light emitter between 5 to 50 mm.

30. The method of claim 1, wherein said known relative positions are fixed.

* * * * *